United States Patent
Sanders et al.

(10) Patent No.: US 10,736,771 B2
(45) Date of Patent: Aug. 11, 2020

(54) METHODS AND DEVICES FOR TREATING SLEEP APNEA

(71) Applicant: Linguaflex, Inc., Davie, FL (US)

(72) Inventors: Ira Sanders, Oakland, NJ (US); Cliff Dwyer, Weston, FL (US)

(73) Assignee: Linguaflex, Inc., Pittsburgh, PA (US)

(*) Notice: Subject to any disclaimer, the term of this patent is extended or adjusted under 35 U.S.C. 154(b) by 48 days.

(21) Appl. No.: 15/898,766

(22) Filed: Feb. 19, 2018

(65) Prior Publication Data
US 2018/0168852 A1    Jun. 21, 2018

Related U.S. Application Data

(63) Continuation of application No. 13/124,365, filed as application No. PCT/US2009/060991 on Oct. 16, 2009, now Pat. No. 9,925,086.

(60) Provisional application No. 61/196,257, filed on Oct. 16, 2008.

(51) Int. Cl.
*A61F 5/56* (2006.01)
*A61B 17/00* (2006.01)

(52) U.S. Cl.
CPC .... *A61F 5/566* (2013.01); *A61B 2017/00349* (2013.01)

(58) Field of Classification Search
CPC ..... A61B 1/24; A61B 17/24; A61B 2017/248; A61F 2005/563; A61F 5/566; A61F 5/56
See application file for complete search history.

(56) References Cited

U.S. PATENT DOCUMENTS

| | | |
|---|---|---|
| 3,517,669 A | 6/1970 | Buono et al. |
| 3,659,612 A | 5/1972 | Shiley et al. |
| 4,254,774 A | 3/1981 | Boretos |
| 4,335,723 A | 6/1982 | Patel |
| 4,387,879 A | 6/1983 | Tauschinski |

(Continued)

FOREIGN PATENT DOCUMENTS

| | | |
|---|---|---|
| DE | 19756956 C1 | 7/1999 |
| JP | 2000060862 A | 2/2000 |

(Continued)

OTHER PUBLICATIONS

Doghramji et al., "Predictors of Outcome for Uvulopalatopharnygoplasty", Laryngoscope, 1995, vol. 105, pp. 311-314.

(Continued)

*Primary Examiner* — Julianna N Harvey
(74) *Attorney, Agent, or Firm* — The Webb Law Firm

(57) ABSTRACT

An implantable tissue retractor for treatment of a breathing disorder and related methods. The implantable tissue retractor comprises a shaft sized for insertion into a soft tissue located in a patient's oral cavity or pharynx. The implantable tissue retractor also comprises a retractor member at or near a first end of the shaft. The implantable tissue retractor also comprises a removable coupler connected at or near a second end of the shaft. At least one of a portion of the shaft or the retractor member is positionable on a surface of the soft tissue. At least one of the shaft, retractor member, or removable coupler is adjustable to vary a force to prevent a deformation of at least a portion of the soft tissue to prevent obstruction of the patient's airway.

12 Claims, 33 Drawing Sheets

(56) References Cited

U.S. PATENT DOCUMENTS

| | | | |
|---|---|---|---|
| 4,704,111 A | 11/1987 | Moss | |
| 4,796,612 A | 1/1989 | Reese | |
| 4,907,602 A | 3/1990 | Sanders | |
| 4,981,477 A | 1/1991 | Schon et al. | |
| 5,109,850 A | 5/1992 | Blanco et al. | |
| 5,190,053 A | 3/1993 | Meer | |
| 5,250,049 A * | 10/1993 | Michael | A61B 17/683 411/908 |
| 5,364,410 A | 11/1994 | Failla et al. | |
| 5,376,110 A | 12/1994 | Tu et al. | |
| 5,443,477 A | 8/1995 | Marin et al. | |
| 5,464,395 A | 11/1995 | Faxon et al. | |
| 5,470,308 A * | 11/1995 | Edwards | A61B 10/0233 604/22 |
| 5,480,420 A | 1/1996 | Hoegnelid et al. | |
| 5,498,247 A | 3/1996 | Brimhall | |
| 5,591,216 A | 1/1997 | Testerman et al. | |
| 5,620,408 A * | 4/1997 | Vennes | A61B 1/00154 128/200.26 |
| 5,694,922 A | 12/1997 | Palmer | |
| 5,792,067 A | 8/1998 | Karell | |
| 5,797,913 A | 8/1998 | Dambreville et al. | |
| 5,843,021 A | 12/1998 | Edwards et al. | |
| 5,954,050 A | 9/1999 | Christopher | |
| 5,961,440 A | 10/1999 | Schweich, Jr. et al. | |
| 5,976,109 A | 11/1999 | Heruth | |
| 5,980,557 A * | 11/1999 | Iserin | A61F 2/0811 606/213 |
| 5,988,171 A | 11/1999 | Sohn et al. | |
| 5,989,244 A | 11/1999 | Gregory et al. | |
| 5,997,567 A | 12/1999 | Cangelosi | |
| 6,013,728 A | 1/2000 | Chen et al. | |
| 6,132,384 A | 10/2000 | Christopherson et al. | |
| 6,152,935 A | 11/2000 | Kammerer et al. | |
| 6,161,541 A | 12/2000 | Woodson | |
| 6,251,059 B1 | 6/2001 | Apple et al. | |
| 6,267,775 B1 | 7/2001 | Clerc et al. | |
| 6,408,851 B1 | 6/2002 | Karell | |
| 6,409,720 B1 | 6/2002 | Hissong et al. | |
| 6,439,238 B1 | 8/2002 | Brenzel et al. | |
| 6,458,079 B1 | 10/2002 | Cohn et al. | |
| 6,523,541 B2 | 2/2003 | Knudson et al. | |
| 6,546,936 B2 | 4/2003 | Knudson et al. | |
| 6,547,787 B1 | 4/2003 | Altman et al. | |
| 6,558,321 B1 | 5/2003 | Burd et al. | |
| 6,601,584 B2 | 8/2003 | Knudson et al. | |
| 6,610,065 B1 | 8/2003 | Branch et al. | |
| 6,618,627 B2 | 9/2003 | Lattner et al. | |
| 6,636,767 B1 | 10/2003 | Knudson et al. | |
| 6,636,769 B2 | 10/2003 | Govari et al. | |
| 6,742,524 B2 | 6/2004 | Knudson et al. | |
| 6,764,446 B2 | 7/2004 | Wolinsky et al. | |
| 6,921,401 B2 | 7/2005 | Lerch et al. | |
| 6,955,172 B2 | 10/2005 | Nelson et al. | |
| 7,146,981 B2 | 12/2006 | Knudson et al. | |
| 7,188,627 B2 | 3/2007 | Nelson et al. | |
| 7,237,554 B2 | 7/2007 | Conrad et al. | |
| 7,337,781 B2 | 3/2008 | Vassallo | |
| 2001/0050084 A1 | 12/2001 | Knudson et al. | |
| 2001/0050085 A1 | 12/2001 | Knudson et al. | |
| 2001/0054428 A1 | 12/2001 | Knudson et al. | |
| 2002/0189622 A1 | 12/2002 | Cauthen, III et al. | |
| 2003/0069626 A1 | 4/2003 | Lattner et al. | |
| 2003/0091328 A1 | 5/2003 | Ishii et al. | |
| 2003/0125743 A1 * | 7/2003 | Roman | A61B 17/688 606/324 |
| 2004/0045556 A1 | 3/2004 | Nelson et al. | |
| 2005/0004417 A1 | 1/2005 | Nelson et al. | |
| 2005/0092332 A1 | 5/2005 | Conrad et al. | |
| 2005/0092334 A1 | 5/2005 | Conrad et al. | |
| 2006/0201519 A1 | 9/2006 | Frazier et al. | |
| 2006/0207606 A1 | 9/2006 | Roue et al. | |
| 2006/0235264 A1 | 10/2006 | Vassallo | |
| 2007/0078430 A1 | 4/2007 | Adams | |
| 2007/0119463 A1 | 5/2007 | Nelson et al. | |
| 2007/0144534 A1 | 6/2007 | Mery et al. | |
| 2007/0144539 A1 | 6/2007 | van der Burg et al. | |
| 2007/0233151 A1 * | 10/2007 | Chudik | A61B 17/1764 606/96 |
| 2007/0261701 A1 | 11/2007 | Sanders | |
| 2007/0288057 A1 | 12/2007 | Kuhnel | |
| 2008/0021485 A1 | 1/2008 | Catanese, III et al. | |
| 2008/0023012 A1 | 1/2008 | Dineen et al. | |
| 2008/0027560 A1 | 1/2008 | Jackson et al. | |
| 2008/0066766 A1 | 3/2008 | Paraschac et al. | |
| 2008/0066767 A1 | 3/2008 | Paraschac et al. | |
| 2008/0078412 A1 | 4/2008 | Buscemi et al. | |
| 2008/0139877 A1 | 6/2008 | Chu et al. | |
| 2009/0177027 A1 | 7/2009 | Gillis | |

FOREIGN PATENT DOCUMENTS

| | | | |
|---|---|---|---|
| JP | 2001145646 A | 5/2001 | |
| JP | 2008526286 A | 7/2008 | |
| WO | 9221291 A2 | 12/1992 | |
| WO | 9721385 A1 | 6/1997 | |
| WO | 9900058 A1 | 1/1999 | |
| WO | 9932057 A1 | 7/1999 | |
| WO | 0029063 A1 | 5/2000 | |
| WO | 03092765 A2 | 11/2003 | |
| WO | 2004064729 A2 | 8/2004 | |
| WO | 2005044158 A1 | 5/2005 | |
| WO | 2005051292 A2 | 6/2005 | |
| WO | 2005082452 A1 | 9/2005 | |
| WO | 2005110280 A2 | 11/2005 | |
| WO | 2007064908 A2 | 6/2007 | |
| WO | 2007092865 A2 | 8/2007 | |

OTHER PUBLICATIONS

Freidman et al., "Minimally Invasive Single-Stage Multilevel Treatment for Obstructive Sleep Apnea/Hypopnea Syndrome", The Laryngoscope, Oct. 2007, vol. 117, pp. 1859-1863.

Horner, "Motor control of the Pharyngeal Musculature and Implications for the Pathogenesis of Obstructive Sleep Apnea", Sleep, 1996, vol. 19, pp. 827-853.

Krespi et al., "Hyoid Suspension for Obstructive Sleep Apnea", Operative Techniques in Otolaryngology—Head and Neck Surgery, Jun. 2002, vol. 13:2, pp. 144-149.

Loube, "Technologic Advances in the Treatment of Obstructive Sleep Apnea Syndrome", Chest, 1999, vol. 116, pp. 1426-1433.

Mickelson et al., "Midline Glossectomy and Epiglottidectomy for Obstructive Sleep Apnea Syndrome", Laryngoscope, 1997, vol. 107, pp. 614-619.

Mintz et al., "A Modified Geniotomy Technique for Obstructive Sleep Apnea Syndrome", J. Oral Maxillofac Surgery, 1995, vol. 53, pp. 1226-1228.

Nordgard et al., "One-year Results: Palatal Implants for the Treatment of Obstructive Sleep Apnea", Otolaryngology—Head and Neck Surgery, 2007, vol. 136, pp. 818-822.

Powell et al., "Radiofrequency Volumetric Tissue Reduction of the Palate in Subjects with Sleep-Disordered Breathing", Chest, 1998, vol. 113, pp. 1163-1174.

Proffit, "Muscle Pressures and Tooth Position: A Review of Current Research", Australian Orthodontic Journal, 1973, pp. 104-108.

Riley et al., "Surgery and Obstructive Sleep Apnea: Long-Term Clinical Outcomes", Operative Techniques in Otolaryngology—Head and Neck Surgery, Mar. 2007, vol. 122:3, pp. 415-421.

Rotunda et al., "Detergent Effects of Sodium Deoxycholate Are a Major Feature of an Injectable Phosphatidylcholine Formulation Used for Localized Fat Dissolution", Dermatologic Surgery, 2004, vol. 30(7), pp. 1001-1008.

Strollo et al., "Medical Therapy for Obstructive Sleep Apnea-Hypopnea Syndrome", Principles and Practice of Sleep Medicine, 4th ed., 2005, pp. 1053-1065.

Treiber et al., "Breast Deformity Produced by Morphea in a Young Girl", Cutis, 1994, vol. 54, pp. 267-268.

(56) References Cited

OTHER PUBLICATIONS

Vicente et al., "Tongue-Base Suspension in Conjunction with Uvulopalatopharyngoplaty for Treatment of Severe Obstructive Sleep Apnea; Long-Term Follow-Up Results", Laryngoscope, Jul. 2006, vol. 116, pp. 1223-1227.
Woodson "A Tongue Suspension Suture for Obstructive Sleep Apnea and Snorers", Operative Techniques in Otolaryngology—Head and Neck Surgery, Mar. 2001, vol. 124:3, pp. 297-303.
Woodson et al., "A Randomized Trial of Temperature-Controlled Radiofrequency, Continuous Positive Airway Pressure, and Placebo for Obstructive Sleep Apnea Syndrome", Otolaryngology—Head and Neck Surgery, Jun. 2003, vol. 128:6, pp. 848-861.
Woodson et al., "Pharyngeal Suspension Suture with Repose Bone Screw for Obstructive Sleep Apnea", Otolaryngology—Head and Neck Surgery, Mar. 2000, vol. 122:3, pp. 395-401.
Argamaso, "Glossopexy for Upper Airway Obstruction in Robin Sequence", Cleft Palate-Craniofacial Journal, 1992, pp. 232-238, vol. 29(3).
Darrow et al., "Management of Sleep-Related Breathing Disorders in Children", Operative Techniques in Otolaryngology—Head and Neck Surgery, 2002, pp. 111-118, vol. 13(2).
De Lorenzi et al., "Glossopexy over tracheostomy in the treatment of glossoptosis", Eur J Plast Surg, 2001, pp. 25-27, vol. 24.
Fearon et al., "The Management of Long Term Airway Problems in Infants and Children", Ann Otol, 1971, pp. 669-677, vol. 80.
Morgan et al., "Surgical Management of Macroglossia in Children", Arch Otolaryngol Head Neck Surg, 1996, pp. 326-329, vol. 122.
Routledge, "The Pierre-Robin Syndrome: A Surgical Emergency in the Neonatal Period", British Journal of Plastic Surgery, Oct. 1960, pp. 204-218.

\* cited by examiner

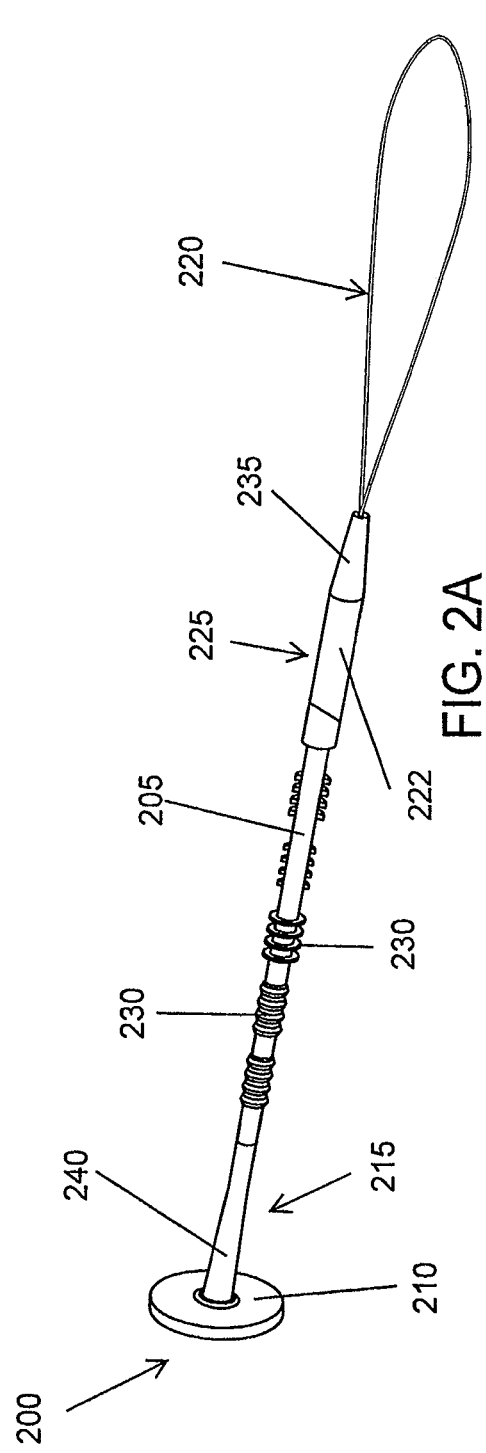
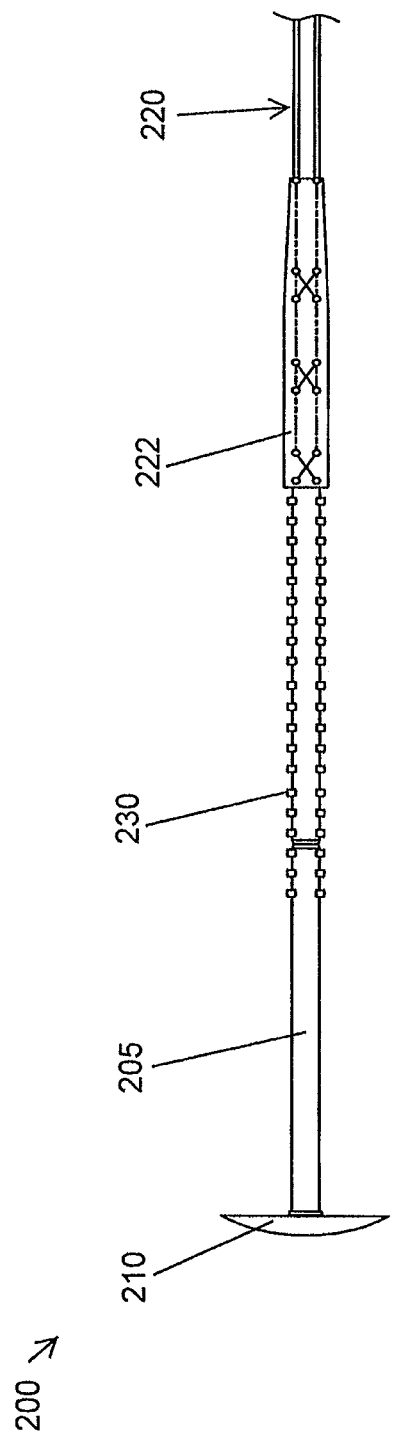

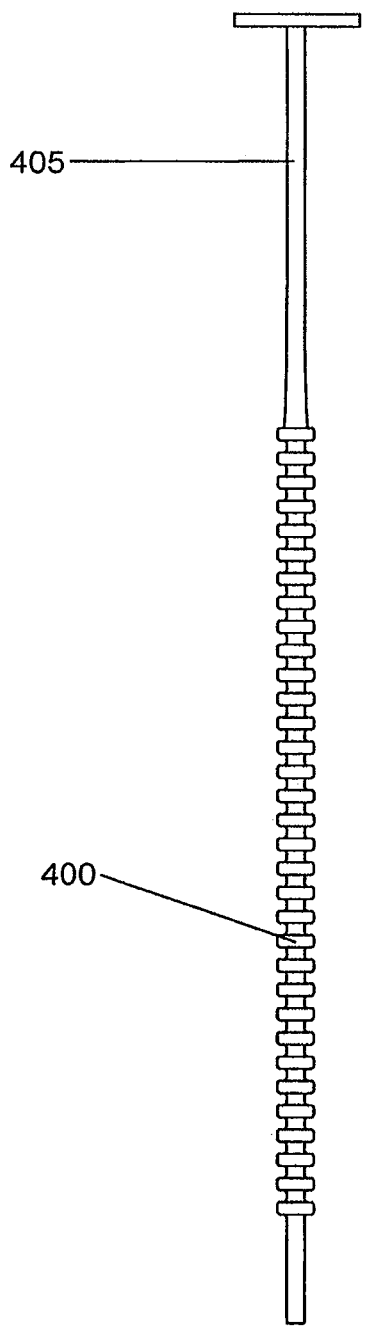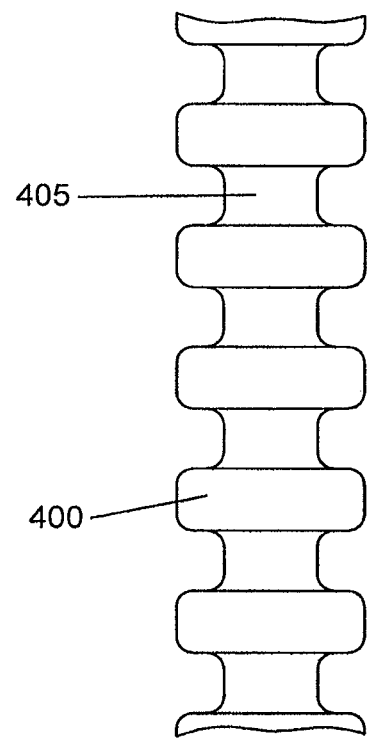
FIG. 4A
FIG. 4B

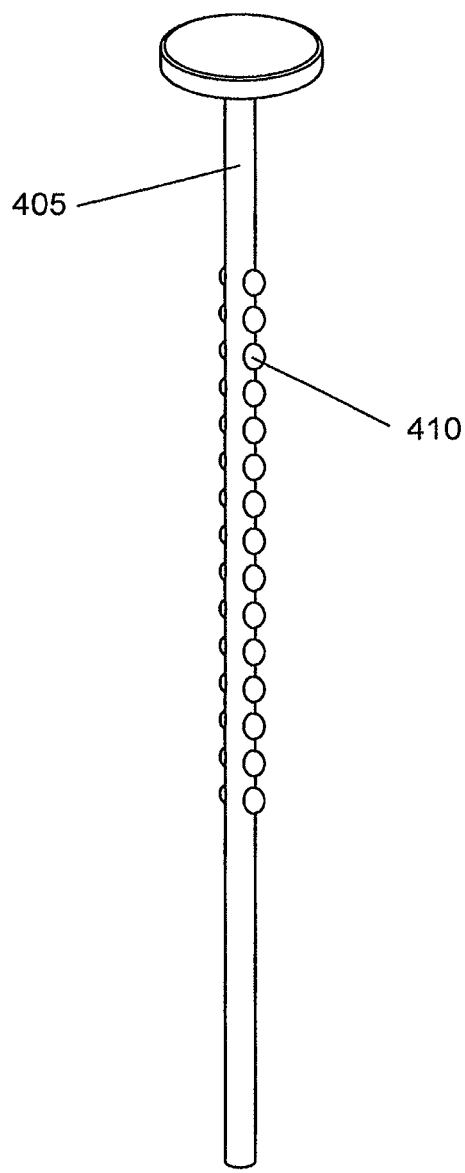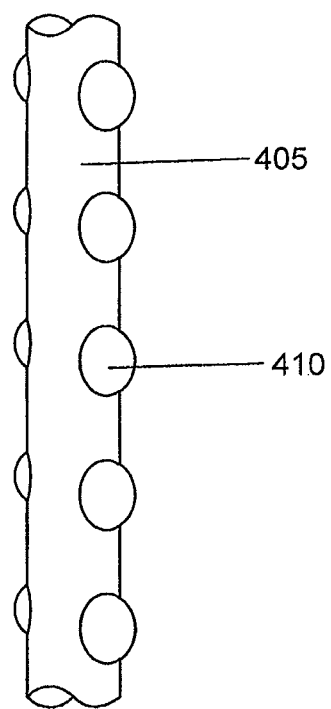
FIG. 4C
FIG. 4D

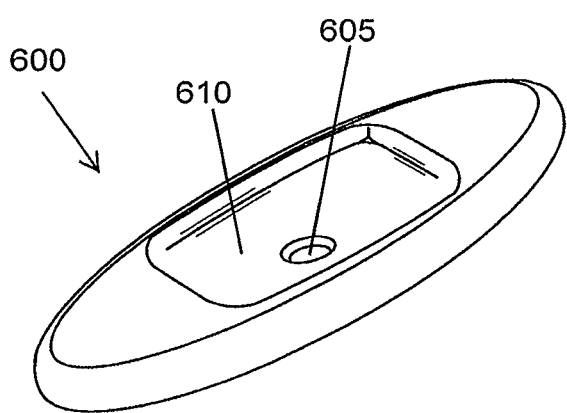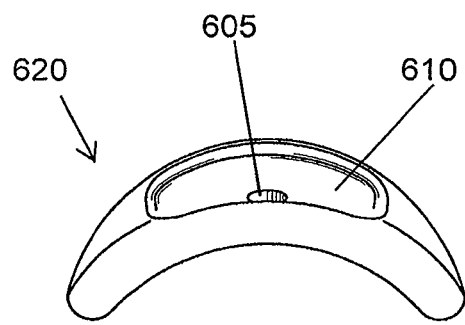
FIG. 6A
FIG. 6B

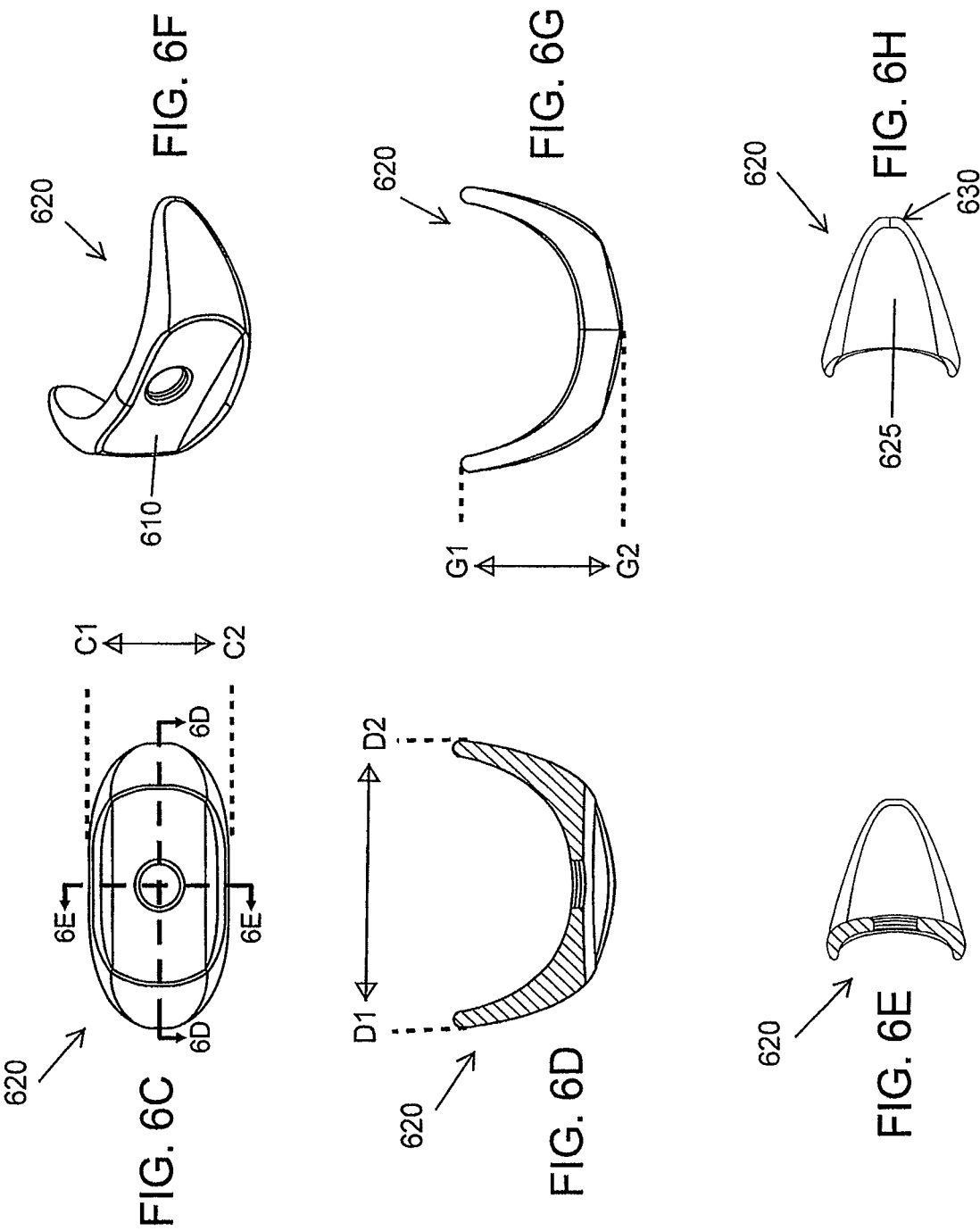

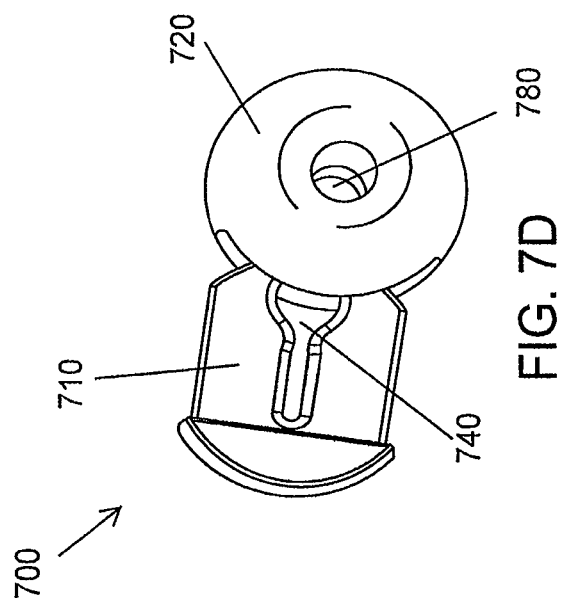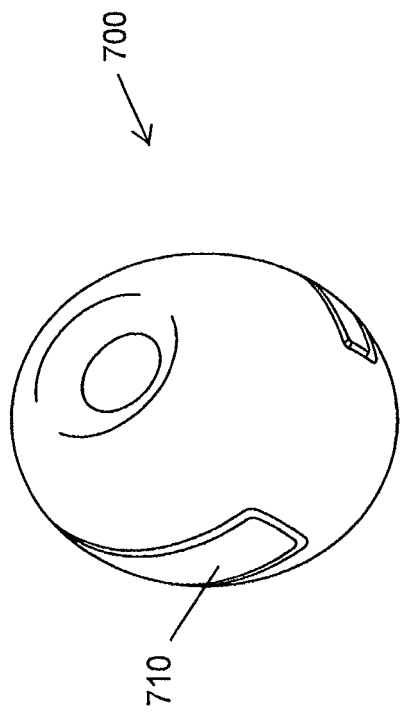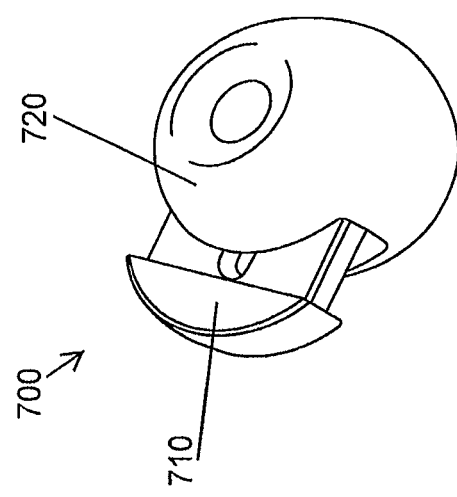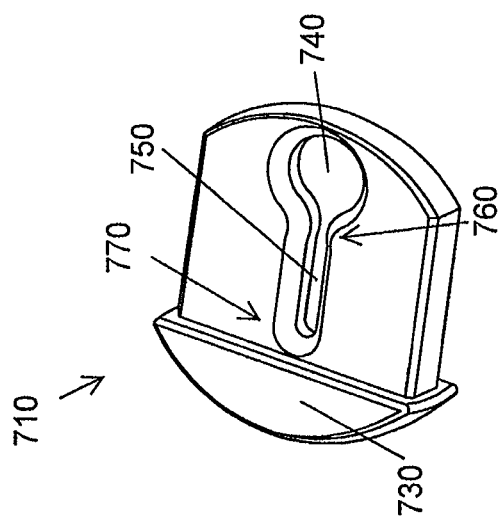

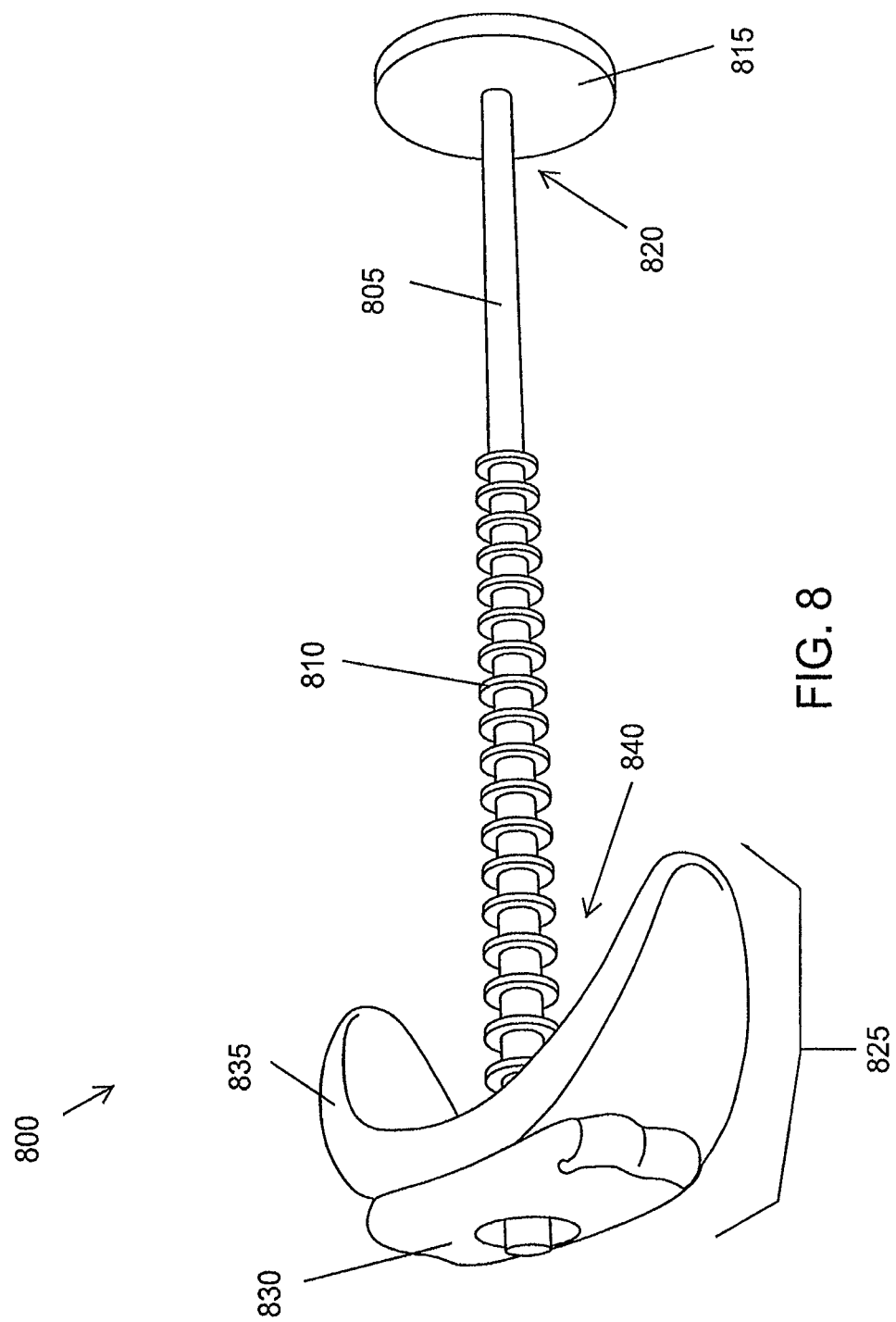

METHODS AND DEVICES FOR TREATING SLEEP APNEA

CROSS-REFERENCE TO RELATED APPLICATIONS

This application is a continuation of U.S. patent application Ser. No. 13/124,365, filed on Jun. 1, 2011, which is a National Phase Application of International Application No. PCT/US2009/060991, filed on Oct. 16, 2009, which claims the benefit of and priority to U.S. Provisional Patent Application No. 61/196,257, filed on Oct. 16, 2008. The disclosures of the above applications are incorporated herein by reference in their entirety.

TECHNICAL FIELD

The present invention relates to devices and methods for the treatment of obstructive sleep apnea syndrome. More specifically, the present invention relates to the treatment of obstructive sleep apnea by retraction of soft tissue in the oral cavity or pharynx.

BACKGROUND

Snoring, upper airway resistance syndrome, and obstructive sleep apnea syndrome ("OSAS") are all breathing disorders related to narrowing of the upper airway during sleep. Approximately 18 million Americans have sleep disordered breathing, but fewer than 50% are presently diagnosed. More than 50% of Americans over age 65 have sleep difficulties, and prevalence of sleep problems will therefore increase as the over-65 population increases. Each year, sleep disorders, sleep deprivation, and excessive daytime sleepiness add approximately $16 billion annually to the cost of health care in the U.S., and result in $50 billion annually in lost productivity.

Sleep disorders are largely caused by too much soft tissue in the throat. Humans are unique because their upper airway has a curved shape, an anatomical change that is related to the evolution of human speech. As a result, the upper airway on humans is more flexible than other species and is more prone to collapse under negative pressure. When awake, a certain amount of tone is present in upper airway muscles to prevent this collapse. However, during sleep muscle tone decreases in upper airway muscles and in certain susceptible individuals this relaxation allows the airway to collapse.

The upper airway refers to the air filled spaces between the nose and the larynx, and their surrounding soft tissue boundaries. For sleep disorders, the most relevant part of the upper airway is the air cavity called the pharynx.

The soft palate and the tongue are most susceptible to collapse because they are very flexible. The soft palate acts as a barrier between the mouth and the nose. The tongue is the largest muscular organ of the upper airway and is anatomically divided into a blade, body and base. Most of the tongue's curve is at the junction of the tongue body and base.

When the tone of the soft palate and tongue decreases during sleep, these structures become quite flexible and distensible. Without the normal muscle tone that keeps them in place, they tend to collapse at relatively low negative pressures. Although muscles relax throughout the body during sleep, many of the respiratory muscles remain active. Specifically, the major muscle that pulls the tongue forward, the genioglossus muscle, has been reported to show decreased activity during sleep, although it is active during obstructive apneas. Normally, the genioglossus is capable of moving the tongue forward and even projecting it out of the mouth. Why the genioglossus muscle fails to prevent obstructions has not been explained.

During inspiration, the chest wall expands and causes negative pressure to draw air into the nose and mouth and past the pharynx into the lungs. This negative pressure causes upper airway soft tissue to deform, further narrowing the airway. If the airway narrows enough, the air flow becomes turbulent causing the soft palate to vibrate. The vibration of the soft palate produces the sound known as snoring. Snoring is extremely common, effecting up to 50% of men and 25% of women. By itself, snoring is not a medical problem although it can be a tremendous problem for the snorer's bed partner and a major cause of marital strain.

A small amount of decreased airflow or brief obstructions occurs in all humans during sleep. These episodes are counted as medically significant if airflow is decreased more than 50% of normal (hypopnea) or if airflow is obstructed for more than 10 seconds (apnea). The number of apneas and hypopneas that occur during each hour of sleep is measured to diagnose the severity of the sleep disorder. These episodes of hypopnea or apnea often cause some degree of arousal during sleep. Although the patient does not awaken to full consciousness, the sleep pattern is disturbed causing the patient to feel sleepy during the day. If the frequency of hypopnea or apnea is more than 5 episodes per hour it is called upper airway resistance syndrome. These patients often show symptoms related to the sleep disruption. Specifically, these patients are excessively sleepy during the day. In addition, more subtle symptoms such as depression and difficulty concentrating are also common.

Technically, the diagnosis of OSAS is defined as an average of more than 10 episodes of hyponea or apnea during each hour of sleep. Although the airway is obstructed, the patient makes repeated and progressively more forceful attempts at inspiration. These episodes are largely silent and characterized by movements of the abdomen and chest wall as the patient strains to bring air into the lungs. Episodes of apnea can last a minute to more, and during this time the oxygen levels in the blood decrease. Finally, either the obstruction is overcome, usually producing a loud snore, or the patient awakes with the feeling of choking.

Very common symptoms in OSAS patients are morning headaches and acid reflux. During airway obstructions, the forceful attempts to inspire air can cause tremendous negative pressure in the chest. These high negative pressures can draw acid up the esophagus from the stomach. The acid can travel all the way into the mouth and cause inflammation of the vocal cords and nasal mucosa. The presence of the acid in the upper airway causes reflex bronchoconstriction in the lung that is similar to an asthma attack. If even a small amount of acid enters the lung it can cause the vocal folds to close tightly and itself cause a prolonged apnea called laryngospasm. In many patients the repeated stretching of the espophageal sphincter causes chronic changes and these patients can have acid reflux during the day.

Although OSAS occurs in both children and adults the cause and treatment are very different. OSAS in children almost always occurs when the child has large tonsils, and tonsillectomy cures the condition. Tonsils naturally decrease in size with age and are rarely a problem in adults. Instead, susceptible adults usually have enlargement of their tongues, soft palate, and/or pharyngeal walls. This enlargement is mostly due to fat deposits within these structures.

Adult sleep disorders are difficult to treat for a variety of reasons. The upper airway is a very mobile structure that performs the critical functions of swallowing and speech. These functions are easily compromised by surgical procedures or other interventions. In addition, the upper airway also has a large amount of sensory innervation that causes reflexes such as gagging and coughing. Theoretically, a physical stent that is placed in the oral cavity and pharynx would be completely effective in relieving sleep apnea. When a patient is totally unconscious, such as when they are anesthetized for surgery, the airway can be stented open by placing a curved oral tube into the mouth and pharynx. In addition, endotracheal tubes establish a secure airway for artificial ventilation. However, after anesthesia wears off, patients immediately sense and react to the foreign objects in their throats and expel them. Therefore, devices such as oral and endotrachael tubes, or anything similar, cannot be used for the treatment of OSAS.

Although physical stents cannot be used for OSAS, an indirect way of stenting the upper airway with positive air pressure is the most commonly prescribed treatment for OSAS. This method is called continuous positive airway pressure ("CPAP"). CPAP requires the use of a mask tightly attached around the nose and connected to a respirator. The exact amount of positive pressure is different for each patient and must be set by overnight testing using multiple pressures. The positive pressure acts like a stent to keep the airway open. CPAP is not a cure but a therapy that must be used every night. Although many OSAS patients are helped by CPAP it is not comfortable for the patient or their bed partner. Patients often cannot tolerate the claustrophobic feeling of a mask tightly attached to their face. In addition, there are often many technical problems with maintaining a proper seal of the mask to the face. For these reasons up to half of all patients who are prescribed CPAP stop using it within 6 months.

FIG. 1A is a schematic illustration of a prior art dental appliance 100. The dental appliance 100 is worn like a retainer and requires nightly compliance by the patient. The dental appliance 100 has an upper dental plate 102 and a lower dental plate 103. The dental appliance 100 also contains a fin-coupling component 105 that allows the mouth to open and close. The dental appliance 100 repositions the lower jaw slightly down and forward relative to the neutral position. This repositioning of the lower jaw forces the tongue to move further away from the back of the airway. Dental appliances generally have minimal efficacy.

FIG. 1B is a schematic illustration of a prior art Repose system 120. The Repose procedure is performed under general anesthesia and a screw (not shown) is inserted at the base of the mandible. The screw contains attachments for a permanent suture 125 that is tunneled under the mucosa of the floor of the mouth to the back of the tongue, then passed across the width of the tongue base, and brought back to attach to a metal hook (not shown) screwed into the bone of the mandible. The entire suture is located within the soft tissue of the tongue. The suture 125 is tightened to displace the tongue base forward, and caution must be observed to prevent excess tension leading to necrosis of tissue. A quantitative measurement of tension is not performed. Tension is estimated by a surgeon. Unfortunately, studies of the Repose procedure show that it is ineffective at eliminating OSAS. Only 1 of 15 patients was cured of OSAS while 2 patients had to have the suture removed due to pain and swelling.

FIG. 1C is a schematic illustration of a prior art Uvulopalatopharyngoplasty ("UPPP") 130. UPPP is one type of surgical procedure that is available to shrink or stiffen the soft palate. UPPP excises excess soft tissue 135 of the pharyngeal walls and soft palate with a surgical scalpel. Because so much mucosa of the pharyngeal area is traumatized during a UPPP there is a large amount of post operative swelling and severe pain. In selected patients who snore but have no obstructions more limited versions of the UPPP can be done with lasers or electrical cautery.

One problem with some known devices and methods for the treatment of obstructive sleep apnea is that prior approaches have minimal or limited efficacy. Another problem is that prior approaches can be highly invasive, requiring significant, obtrusive, sometimes irreversible surgery, which can also lead to a high risk of infection. Another problem with some prior art solutions is that patients experience significant foreign body sensations when devices are placed in the patients' oral cavity as well as a negative social stigma when the foreign bodies are visible to the general population.

Accordingly, a need exists for improved methods and devices for the treatment of obstructive sleep apnea.

SUMMARY

The invention overcomes these and other problems by providing a minimally invasive treatment of obstructive sleep apnea without requiring major surgery. In addition, the invention overcomes the problems of the prior art solutions by providing a device that is easily adjustable and removable and a method of treatment that is entirely reversible. Furthermore, the invention overcomes the problems of the prior art solutions because patients do not experience any foreign body sensations when the device is implanted nor do patients experience any social stigma as the device is invisible to the general public.

The invention, in one aspect, features an implantable tissue retractor for treatment of a breathing disorder. The implantable tissue retractor includes a shaft sized for insertion into a soft tissue located in a patient's oral cavity or pharynx. The implantable tissue retractor also includes a retractor member at or near a first end of the shaft. The implantable tissue retractor also includes a removable coupler connected at or near a second end of the shaft. At least one of a portion of the shaft or the retractor member is positionable on a surface of the soft tissue. At least one of the shaft, retractor member, or removable coupler is adjustable to vary a force to prevent a deformation of at least a portion of the soft tissue to prevent obstruction of the patient's airway.

In some embodiments, the removable coupler comprises a suture, a magnet, a vacuum, an adhesive, a screw, or a hook.

In some embodiments, the shaft has at least one securing feature. In some embodiments, the securing feature comprises a protuberance. In other embodiments, the securing feature comprises a cavity. In other embodiments, the securing feature comprises an aperture. In some embodiments, the securing feature is integrally formed with the shaft.

In some embodiments, the shaft of the implantable tissue retractor is flexible. In some embodiments, the shaft is made from silicon and in other embodiments the shaft is made from stainless steel.

In some embodiments, the implantable tissue retractor further includes an anchor member. In some embodiments, the anchor member comprises a locking member and a pad. In some embodiments, the pad has a recess. The recess capable of receiving the locking member or the anchor member. In other embodiments, the pad is curved. The pad is capable of contacting the soft tissues located in the patient's oral cavity or pharynx and distributing force across the soft tissue. In some embodiments, the pad is adapted to be removed from the shaft without removing the locking member from the shaft.

In some embodiments, the retractor member of the implantable tissue retractor is disc shaped, rod shaped, triangularly shaped, cross-rod shaped, saddle shaped, half-saddle shaped, oval shaped, or rectangularly shaped. In other embodiments, the retractor member is off center along at least one axis.

In some embodiments, the shaft of the implantable tissue retractor has a first end and a second end. The first end has a first thickness. An intermediate portion is located between the first end and the second end. The intermediate portion has a second thickness. In some embodiments the first thickness is greater than the second thickness. In some embodiments, the intermediate portion is located at or near the removable coupler.

In some embodiments, the shaft of the implantable tissue retractor has a thickness of about 0.1 millimeters to about 5 millimeters.

The invention, in another aspect, features a tissue retractor for treatment of a breathing disorder. The tissue retractor includes a shaft sized for insertion into a soft tissue located in a patient's oral cavity or pharynx. The shaft has at least one securing feature. The tissue retractor also includes a retractor member connected at or near a first end of the shaft. The tissue retractor also includes an anchor member engagable by the at least one securing feature. At least one of the shaft, the retractor member or the anchor member is positionable on a surface of the soft tissue. At least one of the shaft, the retractor member, or the anchor member is adjustable to vary a force that prevents a deformation of at least a portion of the soft tissue to prevent obstruction of the patient's airway.

In some embodiments, the anchor member includes a locking member and a pad. The pad is configured to distribute a force across the soft tissue. In some embodiments, the pad has a recess. The recess is capable of receiving the locking member.

In some embodiments, the securing feature is a protuberance. In other embodiments, the securing feature is a cavity. In other embodiments, the securing feature is an aperture.

In some embodiments, the locking member is a slide lock or a clamshell lock.

In some embodiments, the retractor member is disc shaped, rod shaped, triangularly shaped, cross-rod shaped, saddle shaped, half-saddle shaped, oval shaped, or rectangularly shaped.

In some embodiments, the shaft has a first end and a second end. The first end has a first thickness. An intermediate portion is located between the first end and the second end. The intermediate portion has a second thickness. In some embodiments, the second thickness is less than the first thickness. The first thickness and the second thickness meet at a junction. In some embodiments, the junction is located at or near the anchor member.

The invention, in another aspect, features a tissue retractor holder for implantation of a tissue retractor. The tissue retractor holder includes a handle. The tissue retractor holder also includes a retainer disposed at a distal end of the handle for releasably retaining a removable coupler. The tissue retractor holder also includes a detainer positioned along the handle, the detainer for releasably engaging an implantable tissue retractor. The retainer is adapted to provide a force to a soft tissue of a patient's oral cavity. The force prevents deformation of the soft tissue when an implantation device is inserted into an opposite side of the soft tissue.

In some embodiments, the retainer includes a first forked arm extending from the distal end of the handle. The retainer also includes a second forked arm extending from the distal end of the handle. In some embodiments, a distal end of the first forked arm is connected to a distal end of the second forked arm forming a continuous surface.

In some embodiments, the detainer comprises at least one of a groove, a clamp or a clip.

In some embodiments, the tissue retractor holder further includes a guard disposed at or near the retainer. The guard is configured to impede an excessive progression of an implantation device.

In some embodiments, the handle of the tissue retractor holder is curved at or near where the handle and the retainer are joined.

The invention, in another aspect, features an implantation device for insertion of a tissue retractor. The implantation device includes a shaft having a pointed end and a second end. The implantation device also includes a first mechanical coupler near the pointed end of the shaft. The first mechanical coupler is adapted to couple with a removable coupler of the tissue retractor. The implantation device also includes a handle at the second end.

In some embodiments, the first mechanical coupler comprises a cleft. In other embodiments, the first mechanical coupler comprises a suture, a magnet, a vacuum, an adhesive, a screw, or a hook.

In some embodiments, the removable coupler of the tissue retractor comprises a suture, a magnet, a vacuum, an adhesive, a screw, or a hook.

In some embodiments, the implantation device further includes a releasable locking member located at or near the first mechanical coupler. In some embodiments, the releasable locking member is a sheath. The sheath is sized to fit over the shaft and configured to hinder an unintentional disengagement of a removable coupler of an implantable tissue retractor.

In some embodiments, the handle of the implantation device contains a tension meter. The tension meter is capable of measuring the tension of a shaft of an implantable tissue retractor.

The invention, in another aspect, features a kit for treatment of a breathing disorder. The kit includes an implantable tissue retractor. The implantable tissue retractor includes a shaft sized for insertion into a soft tissue located in a patient's oral cavity or pharynx. The implantable tissue retractor also includes a retractor member disposed at or near a first end of the shaft. The implantable tissue retractor also includes a removable coupler connected at or near a second end of the shaft. The kit also includes a tissue retractor holder. The tissue retractor holder includes a handle. The tissue retractor holder also includes a retention system disposed at a distal end of the handle for temporarily retaining the removable coupler. The tissue retractor holder also includes a detainer positioned on the handle. The detainer is capable of engaging the implantable tissue retractor.

In some embodiments, the kit further includes an implantation device. The implantation device includes a shaft having a pointed end and a second end. The implantation device also includes a mechanical coupler near the pointed end of the shaft. The mechanical coupler is adapted to couple with the removable coupler. The implantation device also includes a handle at the second end.

The invention, in another aspect, features a method for treatment of a breathing disorder. The method includes a) inserting a tissue retractor implantation device into a first location of a soft tissue located in a patient's oral cavity or pharynx. The tissue retractor implantation device includes a mechanical coupler. The method also includes b) inserting a first implantable tissue retractor into the oral cavity or pharynx. The first implantable tissue retractor includes a first shaft, a first retractor member connected at or near a first end of the first shaft, and a first removable coupler disposed at or near a second end of the first shaft. The method also includes c) engaging the first removable coupler with the mechanical coupler of the tissue retractor implantation device. The method also includes d) withdrawing the mechanical coupler of the tissue retractor implantation device to secure at least a portion of the first implantable tissue retractor within the soft tissue. The method also includes e) securing a first anchor member to the second end of the first shaft of the first implantable tissue retractor to secure the first implantable tissue retractor within the soft tissue. The method also includes f) removing the first removable coupler.

In some embodiments, the method further includes establishing an amount of securing force against the soft tissue by adjusting a length of the first shaft between the first retractor member and the anchor member. In some embodiments, the method further includes establishing an amount of securing force against the soft tissue by adjusting a physical characteristic of the first shaft between the first retractor member and the anchor member.

In some embodiments, the amount of securing force is about zero to about 1000 grams. In some embodiments, the amount of securing force is about 5 to about 200 grams. In some embodiments, the amount of securing force is about 10 to about 75 grams. In some embodiments, the amount of securing force is about 25 grams.

In some embodiments, step b) includes using a tissue retractor holder to insert the first implantable tissue retractor into the oral cavity or pharynx. The tissue retractor holder includes a handle, a retainer disposed at a distal end of the handle, and a detainer positioned on the handle, the detainer capable of engaging the implantable tissue retractor.

In some embodiments, the method of further includes g) inserting the tissue retractor implantation device into a second location of a soft tissue located in a patient's oral cavity or pharynx. The tissue retractor implantation device includes a mechanical coupler. The method further includes h) inserting a second implantable tissue retractor into the oral cavity or pharynx. The second implantable tissue retractor includes a second shaft and a second removable coupler disposed at or near a second end of the second shaft. The method further includes i) engaging the second removable coupler. The method further includes j) withdrawing the mechanical coupler of the tissue retractor implantation device to secure at least a portion of the second implantable tissue retractor within the soft tissue. The method further includes k) securing a first end of the second implantable tissue retractor to the first retractor member of the first implantable tissue retractor. The method further includes l) securing a second anchor member to the second end of the second shaft of the second implantable tissue retractor to secure the second implantable tissue retractor within the soft tissue. The method further includes m) removing the second removable coupler.

In some embodiments, the method further includes g) inserting a tissue retractor implantation device into a second location of a soft tissue located in a patient's oral cavity or pharynx. The tissue retractor implantation device includes a mechanical coupler. The method further includes h) inserting a second implantable tissue retractor into the oral cavity or pharynx. The second implantable tissue retractor includes a second shaft, a second retractor member connected at or near a first end of the second shaft, and a second removable coupler disposed at or near a second end of the second shaft. The method further includes i) engaging the second removable coupler. The method further includes j) withdrawing the mechanical coupler of the tissue retractor implantation device to secure at least a portion of the second implantable tissue retractor within the soft tissue. The method further includes k) securing a second anchor member to the second end of the second shaft of the second implantable tissue retractor to secure the second implantable tissue retractor within the soft tissue. The method further includes l) removing the second removable coupler.

The invention, in another aspect, features a method of retensioning a tissue retractor. The method includes locating a tissue retractor within a soft tissue of a patient. The tissue retractor includes a retractor member located at or near a first end of a shaft and an anchor member located at or near a second end of the shaft. The method also includes loosening the anchor member. The method also includes establishing an amount of securing force against the soft tissue by adjusting a length of the shaft between the retractor member and the anchor member. The method also includes resecuring the anchor member to the shaft of the tissue retractor.

In some embodiments, the resecuring step is performed using a second anchor member.

The invention, in another aspect, features a method of replacing a tissue retractor. The method includes locating a first tissue retractor within a soft tissue of a patient. The first tissue retractor includes a first retractor member located at or near a first end of a first shaft and a first anchor member located at or near a second end of the first shaft. The method also includes removing the first anchor member. The method also includes extracting the first tissue retractor from the soft tissue of the patient. A conduit is located where the first tissue retractor was extracted from the soft tissue of the patient. The method also includes implanting a second tissue retractor along the conduit of the soft tissue of the patient. The second tissue retractor includes a second shaft and a second retractor member located at or near a first end of the second shaft. The method also includes establishing an amount of securing force against the soft tissue by adjusting a length of the second shaft. The method also includes securing a second anchor member to the second shaft of the second tissue retractor.

BRIEF DESCRIPTION OF THE DRAWINGS

The foregoing and other objects, features and advantages of the invention, as well as the invention itself, will be more fully understood from the following illustrative description, when read together with the accompanying drawings which are not necessarily to scale.

FIG. 2A is a schematic illustration of an implantable tissue retractor, according an illustrative embodiment of the invention.

FIG. 2B is a side view of an implantable tissue retractor of FIG. 2A, according to an illustrative embodiment of the invention.

FIG. 4A is a schematic illustration of a ridge-type securing feature, according to an illustrative embodiment of the invention.

FIG. 4B is an enlarged view of a ridge-type securing feature from FIG. 4A, according to an illustrative embodiment of the invention.

FIG. 4C is a schematic illustration of a bump-type securing feature, according to an illustrative embodiment of the invention.

FIG. 4D is an enlarged view of a bump-type securing feature from FIG. 4C, according to an illustrative embodiment of the invention.

FIG. 6A is a schematic illustration of a flat anchor pad, according to an illustrative embodiment of the invention.

FIG. 6B is a schematic illustration of a curved anchor pad, according to an illustrative embodiment of the invention.

FIG. 6C is a front view of a curved anchor pad, according to an illustrative embodiment of the invention.

FIG. 6D is a top view of a curved anchor pad, according to an illustrative embodiment of the invention.

FIG. 6E is a side view of a curved anchor pad, according to an illustrative embodiment of the invention.

FIG. 6F is a perspective view of a curved anchor pad, according to an illustrative embodiment of the invention.

FIG. 6G is a top perspective view of a curved anchor pad, according to an illustrative embodiment of the invention.

FIG. 6H is a side perspective view of curved anchor pad, according to an illustrative embodiment of the invention.

FIG. 7A is a schematic illustration of spherical anchor member in an open position, according to an illustrative embodiment of the invention.

FIG. 7B is a schematic illustration of the inner element of a spherical anchor member, according to an illustrative embodiment of the invention.

FIG. 7C is a schematic illustration of a spherical anchor member in a closed position, according to an illustrative embodiment of the invention.

FIG. 7D is a schematic illustration of a preassembled spherical anchor member, according to an illustrative embodiment of the invention.

FIG. 8 is a schematic illustration of a tissue retractor, according to an illustrative embodiment of the invention.

DETAILED DESCRIPTION

Figure 1B:
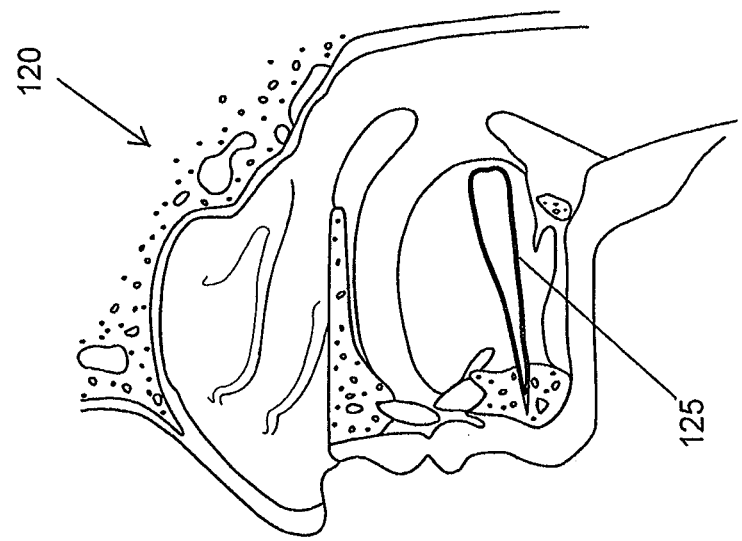
FIG. 1B is a schematic illustration of a prior art repose system.
Figure 1A:
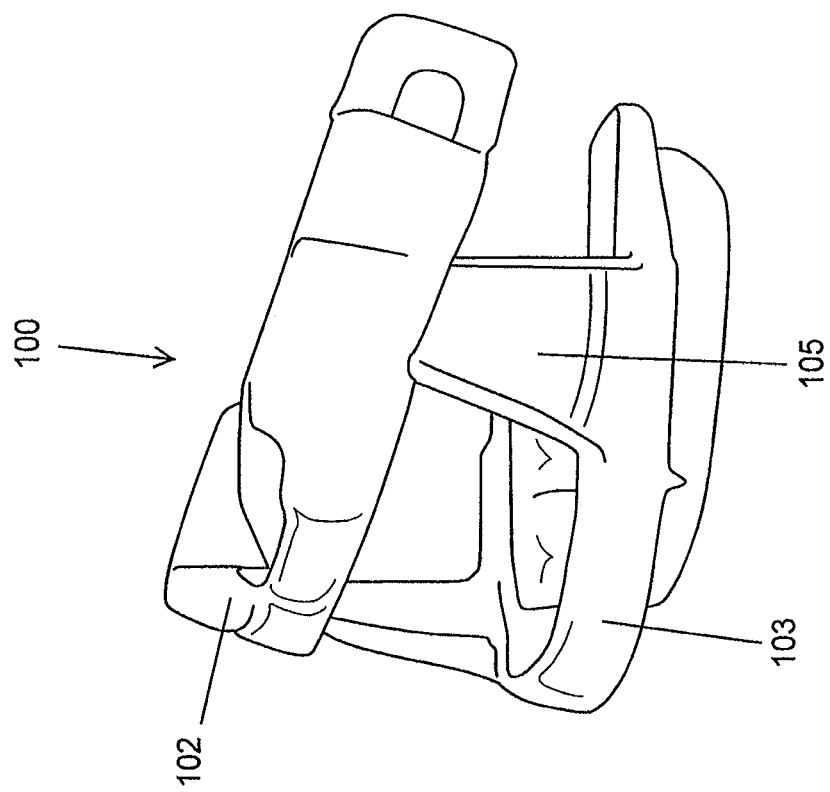
FIG. 1A is a schematic illustration of a prior art dental appliance.
Figure 1C:
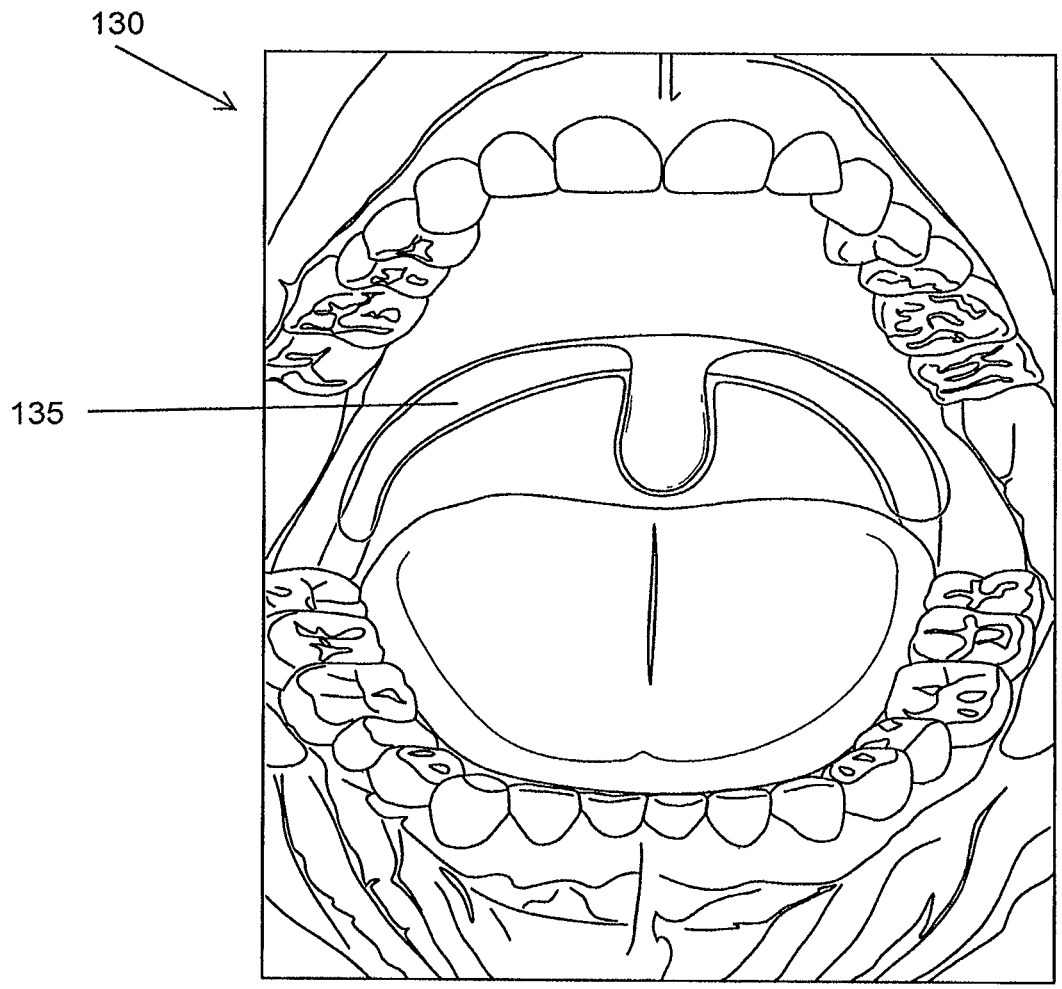
FIG. 1C is a schematic illustration of a prior art Uvulopalatopharyngoplasty.

The invention relates to devices for the treatment of obstructive sleep apnea syndrome. The invention relates to an implantable tissue retractor that provides a forward force along the tongue base mucosa. The forward force unobtrusively prevents the tongue from collapsing and obstructing a patient's airway while the patient is sleeping.

The invention relates to devices to aid in the implantation of the tissue retractor. For example, the invention relates to a tissue retractor holder that holds an implantable tissue retractor in the oral cavity of a patient. The tissue retractor holder can also provide a force along the tongue base mucosa to allow the implantation device to fully penetrate the soft tissue. The force provided by the tissue retractor holder also increases the space within the oral cavity allowing a physician more room to work within the oral cavity.

The invention also relates to methods for the treatment of obstructive sleep apnea syndrome. The invention relates to a reverse threading method for securing an implantable tissue retractor within the soft tissue of a patient. The method can be performed in a doctor's office under local anesthesia and has minimal post procedural discomfort. An implantation device is inserted from the frenulum to the tongue base mucosa. A mechanical coupler on the implantation device engages a removable coupler on an implantable tissue retractor. When the implantation device is withdrawn from the soft tissue, the implantable tissue retractor is secured within the soft tissue.

FIG. 2A is a schematic illustration of an implantable tissue retractor 200, according an illustrative embodiment of the invention. The implantable tissue retractor 200 comprises a shaft 205. The shaft 205 is sized for insertion into a soft tissue located in a patient's oral cavity or pharynx. The shaft 205 can be made of flexible material, for example silicon, or a stiff material, for example stainless steel. In some embodiments, the shaft has a thickness of about 0.1 millimeters to about 5 millimeters. In one embodiment the shaft is cylindrical.

The implantable tissue retractor 200 also comprises a retractor member 210 located at or near a first end 215 of the shaft 205. The implantable tissue retractor 200 also has a removable coupler 220. The removable coupler 220 is connected at or near a second end 225 of the shaft 205. As shown in FIG. 2A, the removable coupler 220 is a suture. However, the removable coupler can comprise a magnet, a vacuum, an adhesive, a screw, a hook, or any other type of coupler.

When the implantable tissue retractor 200 is implanted into a soft tissue located in a patient's oral cavity or pharynx, at least one of a portion of the shaft 205 or the retractor member 210 is positionable on a surface of the soft tissue. In addition, at least one of the shaft 205, the retractor member 210 or the removable coupler 220 is adjustable to vary a force to prevent a deformation of at least a portion of the soft tissue to prevent obstruction of the patient's airway.

FIG. 2B is a side view of an implantable tissue retractor 200, according to an illustrative embodiment of the invention. In some embodiments, the removable coupler 220 is over-molded with the shaft 205 creating an over-molded structure 222. The over-molded structure 222 strengthens the connection between the removable coupler 220 and the shaft 205.

Referring to FIG. 2A, in some embodiments, the retractor member 210 can rest on the tongue base mucosa. The retractor member 210 of the implantable tissue retractor 200 can provide a forward force on the tongue base mucosa thereby preventing tongue collapse and obstruction during sleep. The retractor member 210 can distribute force comfortably to the tongue base. In some embodiments the length of retractor member is about 1 millimeter to about 300 millimeters. In one embodiment the length of the retractor member is about 10 millimeters. In some embodiments the width of the retractor member is about 0.1 millimeters to about 5 millimeters. In one embodiment the width of the retractor member is about 1 millimeter. However, what is comfortable to one patient may not be comfortable to another patient. For example, the dimensions would be smaller if a tissue retractor was implanted in a child and the dimensions would be larger if a tissue retractor was implanted in an adult. In some embodiments, the retractor member 210 has alternative shapes to compensate for the variable tongue shape of sleep apnea patients. Moreover, some patients prefer a translucent retractor member so that the retractor member can be less visible to the general public.

Figure 3A:
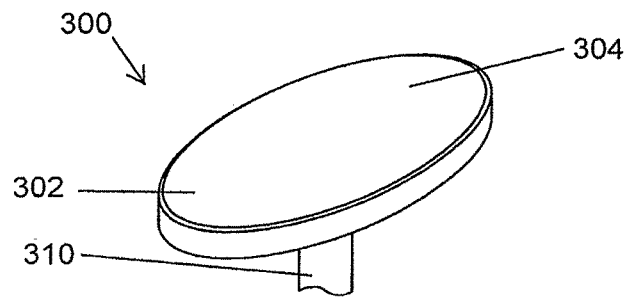
FIG. 3A is a schematic illustration of a retractor member oriented at an angle to a shaft, according to an illustrative embodiment of the invention.

For example, referring to FIGS. 3A to 3J, the retractor member 210 of FIG. 2A can take on various shapes. FIG. 3A is a schematic illustration of a retractor member oriented at an angle 300 to a shaft 310, according to an illustrative embodiment of the invention. When the retractor member is oriented at an angle 300 to the shaft 310, the retractor member 300 distributes a greater force to the downward facing portion 302 of the retractor member 300 and a lesser force to the upward facing portion 304 of the retractor member 300.

Figure 3B:
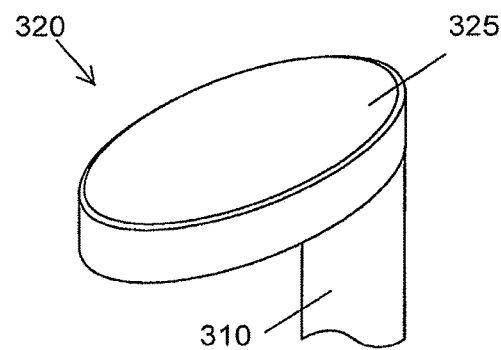
FIG. 3B is a schematic illustration of an off-centered oval head retractor member, according to an illustrative embodiment of the invention.

FIG. 3B is a schematic illustration of an off-centered oval head retractor member 320, according to an illustrative embodiment of the invention. In this embodiment, the shaft 310 is located towards one side of the retractor member 320. In this configuration, the force applied by the off-centered oval head retractor member 320 is distributed to the portion of the soft tissue that is in contact with the downward facing portion 325 of the off-centered oval head retractor member 320.

Figure 3C:
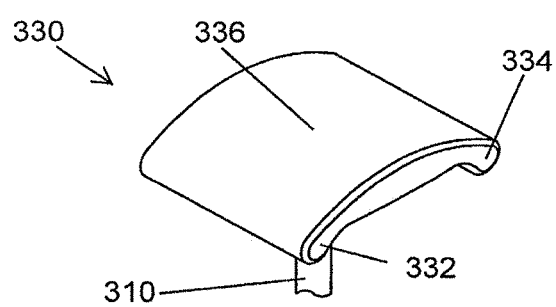
FIG. 3C is a schematic illustration of a saddle-shaped retractor member, according to an illustrative embodiment of the invention.

FIG. 3C is a schematic illustration of a saddle-shaped retractor member 330, according to an illustrative embodiment of the invention. In this embodiment, the shaft 310 is located in the center of the retractor member 330. In this configuration, the force applied by the saddle-shaped retractor member 330 is distributed to the portion of the soft tissue that is in contact with the two downward facing portions 332, 334 of the saddle-shaped retractor member 330. A lesser amount of force is distributed to the portion of the soft tissue that is in contact with the raised portion 336 of the saddle-shaped retractor member 330.

Figure 3D:
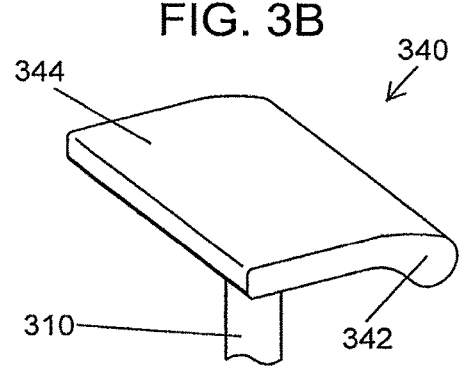
FIG. 3D is a schematic illustration of a half saddle-shaped retractor member, according to an illustrative embodiment of the invention.

FIG. 3D is a schematic illustration of a half saddle-shaped retractor member 340, according to an illustrative embodiment of the invention. In this embodiment, the shaft 310 is located approximately in the center of the retractor member 340. In this configuration, the force applied by the half saddle-shaped retractor member 340 is distributed to the portion of the soft tissue that is in contact with the single downward facing portion 342 of the half saddle-shaped retractor member 340. A lesser amount of force is distributed to the portion of the soft tissue that is in contact with the flat portion 344 of the half saddle-shaped retractor member 340.

Figure 3E:
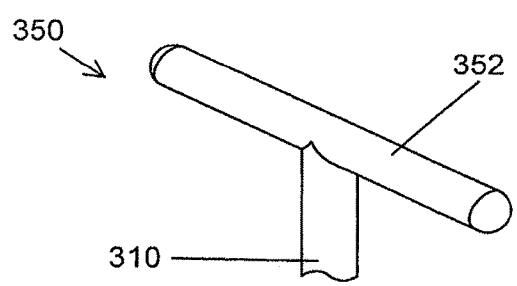
FIG. 3E is a schematic illustration of single rod-shaped retractor member, according to an illustrative embodiment of the invention.

FIG. 3E is a schematic illustration of a single rod-shaped retractor member 350, according to an illustrative embodiment of the invention. In this embodiment, the shaft 310 is located approximately in the center of the retractor member 350. In this configuration, the force applied by the rod-shaped retractor member 350 is distributed approximately evenly along the length of the rod 352.

Figure 3F:
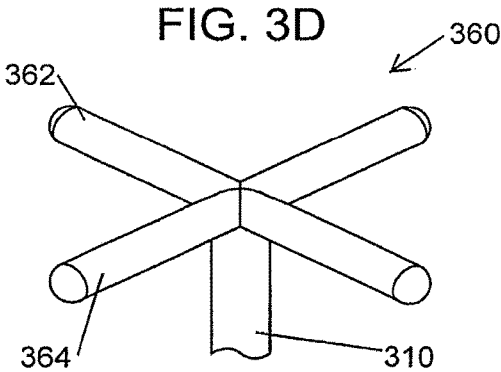
FIG. 3F is a schematic illustration of a crossed rod-shaped retractor member, according to an illustrative embodiment of the invention.

FIG. 3F is a schematic illustration of a crossed rod-shaped retractor member 360, according to an illustrative embodiment of the invention. In this embodiment, the shaft 310 is located approximately in the center of the retractor member 360. In this configuration the force applied by the crossed rod-shaped retractor member 360 is distributed approximately evenly along the first and second rod 362, 364.

Figure 3G:
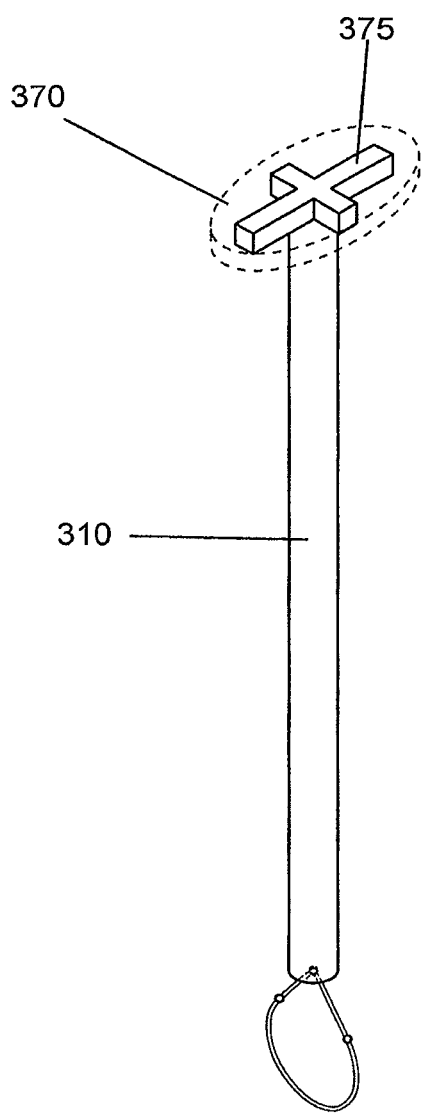
FIG. 3G is a schematic illustration of a retractor member and internal reinforcing member, according to an illustrative embodiment of the invention.

FIG. 3G is a schematic illustration of a retractor member 370 and internal reinforcing member 375, according to an illustrative embodiment of the invention. In this embodiment the shaft 310 is located approximately in the center of the retractor member 370. FIG. 3G shows the retractor member 370 in use with an X-shaped internal reinforcing member 375. Although FIG. 3G shows an oval-shaped retractor member, any shape retractor member can be used (for example, the retractor members of FIGS. 3A-3F). In addition, although FIG. 3G shows an X-shaped internal reinforcing member, any shape internal reinforcing member can be used (for example, the internal reinforcing member of FIGS. 3H-3J). The retractor member 370 can be made from a translucent material, for example silicon, to make sure that the retractor member is not visible to the general public.

Figure 3H:
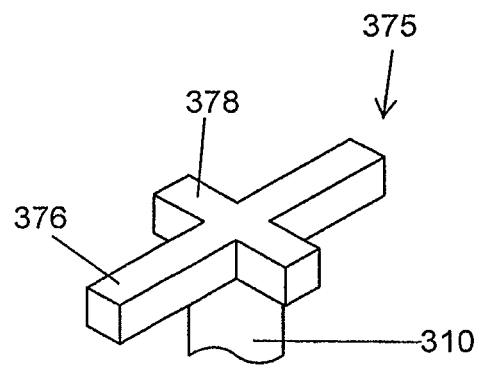
FIG. 3H is a schematic illustration of an X-shaped internal reinforcing member, according to an illustrative embodiment of the invention.

FIG. 3H is a schematic illustration of an X-shaped internal reinforcing member 375, according to an illustrative embodiment of the invention. In this embodiment, the shaft 310 is located approximately in the center of the X-shaped internal reinforcing member 375. In this configuration the force applied by the X-shaped internal reinforcing member 375 is distributed approximately evenly along the long arm 376 and the short arm 378.

Figure 3I:
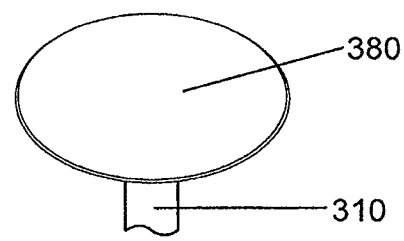
FIG. 3I is a schematic illustration of a disc-shaped internal reinforcing member, according to an illustrative embodiment of the invention.

FIG. 3I is a schematic illustration of a disc-shaped internal reinforcing member 380, according to an illustrative embodiment of the invention. In this embodiment the shaft, 310 is located approximately in the center of the disc-shaped internal reinforcing member 380. In this configuration the force is applied by the disc-shaped internal reinforcing member 380 approximately evenly along the disc. In some embodiments the disc is approximately circular and in other embodiments the disc is approximately oval-shaped.

Figure 3J:
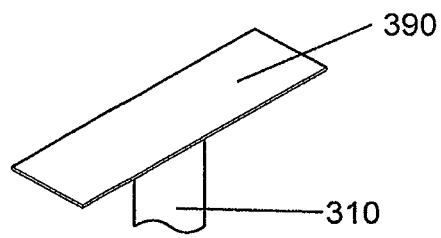
FIG. 3J is a schematic illustration of a rectangular-shaped internal reinforcing member, according to an illustrative embodiment of the invention.

FIG. 3J is a schematic illustration of a rectangular-shaped internal reinforcing member 390, according to an illustrative embodiment of the invention. In this embodiment, the shaft 310 is located approximately in the center of the rectangular-shaped internal reinforcing member 390. In this configuration the force is applied by the rectangular-shaped internal reinforcing member 390 approximately evenly along the rectangle. In some embodiments the internal reinforcing member is approximately rectangular-shaped and in other embodiments the internal reinforcing member is approximately square-shaped.

FIGS. 3A-3F show some examples of the different types of shapes of a retractor member and FIGS. 3J-3I show some examples of the different types of shapes of an internal reinforcing member to a retractor member. In some embodiments the retractor member and internal reinforcing member will have other shapes that are not shown in FIGS. 3A-3J but are still considered to be within the scope of the invention, for example in one embodiment, the retractor member and/or the internal reinforcing member is triangularly shaped. The shape of the retractor member and internal reinforcing member will largely depend on the needs of a specific patient. For example, the shape of tongue can dictate which retractor member and/or internal reinforcing member shape will be most effective in curing OSAS. In addition, the patient's comfort may dictate the specific retractor member and/or internal reinforcing member shape used since patients may find one shape more comfortable than another shape.

The retractor member of the implantable tissue retractor can be made from a variety of different materials. In some embodiments the retractor member is made of a flexible material, for example silicon. A flexible material can be more comfortable to a patient. In other embodiments, the retractor member is made of a rigid material, for example stainless steel. When the retractor member is made from a rigid material the retractor member is prevented from folding up and being pulled into the tongue by the shaft. In addition, the retractor member can be made more resilient to folding by increasing the depth of the retractor member, for example increasing the depth to from about 1 millimeter to about 2 millimeters. The depth of the retractor member can range from about 0.1 millimeters to about 5 millimeters. In some embodiments, the depth of the retractor member can be increased uniformly throughout the entire retractor member. In other embodiments, the depth of the retractor member can be increased only in certain locations. In other embodiments, the retractor member can be made more resilient to folding by using specific shapes, such as a convex shape or a saddle-shape.

In some embodiments, the retractor member can be made more resilient to folding by including stiffer internal components, for example the internal reinforcing member of FIGS. 3G-3J. For example, the retractor member can include a stiffer, disc-shaped internal component that stiffens the retractor member along all axes. In other embodiments, the retractor member can include a stiffer, rod-shaped internal component that stiffens the retractor member along a single, specific axis. In some embodiments, the retractor member is composed of a biocompatible material that is comfortable and non-reactive (for example silicon) while the internal reinforcing member can impart mechanical stiffness, thereby preventing folding of the retractor member. The internal reinforcing member can be made from any material that imparts a greater mechanical stiffness that the retractor member. For example, the retractor member can be made of silicon and the internal reinforcing member can be made of stainless steel.

Referring to FIG. 2A, in some embodiments, to allow for easier locking of the shaft 205 after the implantable tissue retractor 200 is implanted into a patient's oral cavity or pharynx, the shaft 205 can contain at least one securing feature 230. The securing feature 230 can being any shape that allows for easier locking of the shaft 205. In some embodiments, the securing feature is a protuberance (for example a ridge or a bump) and in other embodiments the securing feature is a cavity.

Figure 4E:
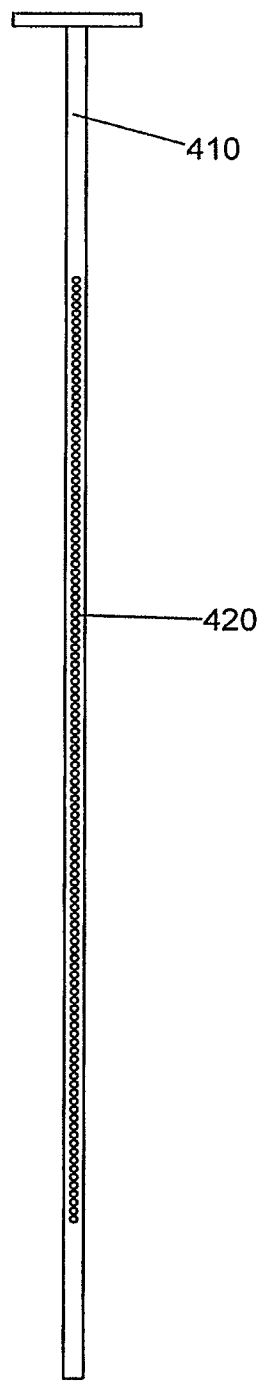
FIG. 4E is a schematic illustration of an aperture-type securing feature, according to an illustrative embodiment of the invention.

FIGS. 4A-4G show some examples of the different embodiments of securing features that can be used to allow for easier locking of the shaft after the implantable tissue retractor is implanted into a patient's oral cavity of pharynx. FIG. 4A is a schematic illustration of a ridge-type securing feature 400, according to an illustrative embodiment of the invention, and FIG. 4B is an exploded view of a ridge-type securing feature 400, according to an illustrative embodiment of the invention. At least one ridge-type securing feature 400 can be located along the shaft 405 of the implantable tissue retractor. In some embodiments, the implantable tissue retractor has one ridge-type securing feature 400 located along the shaft 405. In other embodiments, the implantable tissue retractor has multiple ridge-type securing features 400 located along the shaft 405. In some embodiments, the ridge-type securing feature 400 is partially circumferential, for example, at least part of the ridge is not present and the core shaft surface 405 is continuous.

FIG. 4C is a schematic illustration of a bump-type securing feature 410, according to an illustrative embodiment of the invention, and FIG. 4D is an exploded view of a bump-type securing feature 410, according to an illustrative embodiment of the invention. At least one bump-type securing feature 410 can be located along the shaft 405 of the implantable tissue retractor. In some embodiments, the implantable tissue retractor has one bump-type securing feature 410 located along the shaft 405. In other embodiments, the implantable tissue retractor has multiple bump-type securing features 410 located along the shaft 405.

Figure 4F:
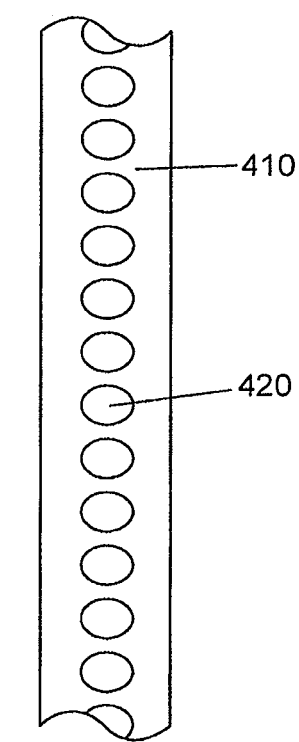
FIG. 4F is an enlarged view of an aperture-type securing feature from FIG. 4E, according to an illustrative embodiment of the invention.

FIG. 4E is a schematic illustration of an aperture-type securing feature 420, according to an illustrative embodiment of the invention, and FIG. 4F is an exploded view of an aperture-type securing feature 420, according to an illustrative embodiment of the invention. At least one aperture-type securing feature 420 can be located along the shaft 405 of the implantable tissue retractor. In some embodiments, the implantable tissue retractor has one aperture-type securing feature 420 located along the shaft 405. In other embodiments, the implantable tissue retractor has multiple aperture-type securing features 420 located along the shaft 405.

Figure 4G:
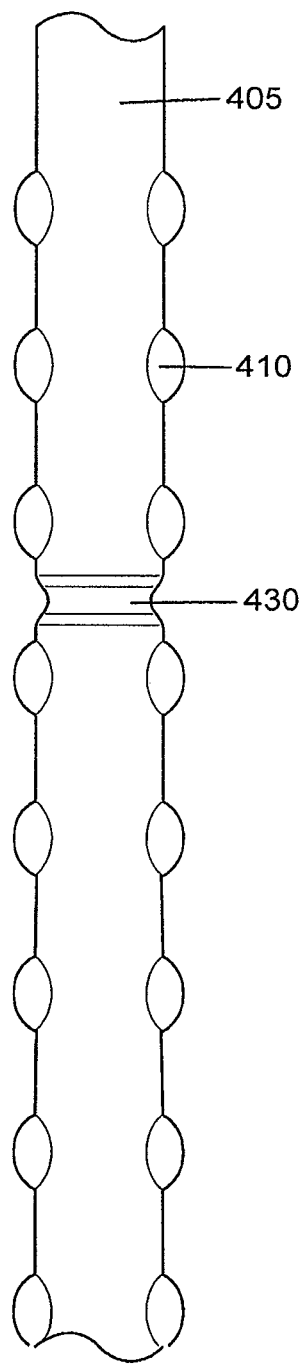
FIG. 4G is a schematic illustration of a cavity-type securing feature, according to an illustrative embodiment of the invention.

FIG. 4G is a schematic illustration of a cavity-type securing feature 430, according to an illustrative embodiment of the invention. At least one cavity-type securing feature 430 can be located along the shaft 405 of the implantable tissue retractor. In some embodiments, the implantable tissue retractor has one cavity-type securing feature 430 located along the shaft 405. In other embodiments, the implantable tissue retractor has multiple cavity-type securing features 430 located along the shaft 405.

FIGS. 4A-4G show some examples of the different embodiments of securing features. In some embodiments the securing feature will have other shapes that are not shown in FIGS. 4A-4G but are still considered to be within the scope of the invention. The securing feature can have any shape will allow an anchor member to easily engage the securing feature. In some embodiments the shaft 405 can contain multiple types of securing features. For example, referring to FIG. 4G, the shaft 405 contains both cavity-type securing features 430 and bump-type securing features 410. Any combination of securing features is within the scope of the invention.

In some embodiments, the securing feature is integrally formed with the shaft of an implantable tissue retractor. For example, the securing feature can be a change in the material of the shaft. If the shaft is made of a silicon material, the shaft could be over-molded with a firmer grade silicon. The firmer grade silicon will act as a securing feature. In other embodiments, the internal component of the shaft is made of a firmer material than the external component of the shaft. For example, a firmer grade silicon can be over-molded with a softer grade silicon.

In some embodiments, the securing features are spaced at equal intervals. In other embodiments, the space between the securing features varies. The securing features can allow a surgeon to adjust the tension of the tissue retractor without having to directly measure the tension. For example, the surgeon can move an anchor member to a securing feature closer to the retractor member to increase the tension of the tissue retractor. The surgeon can also move an anchor member to a securing feature further from the retractor member to decrease the tension of the tissue retractor. In some embodiments, the tension of the shaft at different locations of the securing feature are measured and marked on the implantable tissue retractor before it is implanted. Therefore, when the surgeon moves the anchor member to a particular securing feature, the surgeon will know the tension based on the measurements on the shaft or securing feature.

Referring to FIG. 2A, the shaft 205 can be of uniform thickness throughout its length or it can have variations in its thickness. The variations in the thickness of the shaft 205 serve several different functions. In some embodiments the implantable tissue retractor 200 has a removable coupler 220 that is a suture. The suture can have a thickness of about 0.1 millimeters to about 2 millimeters and the shaft 205 can have a thickness of about 5 millimeters to about 1 millimeter. The abrupt decrease in thickness between the shaft 205 and the removable coupler 220 can cause the implantable tissue retractor 200 to face resistance when the implantable tissue retractor is implanted in the soft tissue of a patient. In addition, the abrupt decrease in the thickness between the shaft 205 and the removable coupler 220 can also lead to the implantable tissue retractor breaking at the abrupt change of thickness when the implantable tissue retractor 200 is bent to be implanted into the soft tissue (see, e.g., FIG. 17). Therefore, in some embodiments the implantable tissue retractor 200 has a lead-in taper 235. The lead-in taper 235 is located at or near the second end 225 of the shaft 205. The lead-in taper 235 can taper from approximately the thickness of the shaft 205 to the thickness of the removable coupler 220. The lead-in taper 235 can cause a gradual increase in thickness as the shaft 205 is implanted into the soft tissue of a patient. The lead-in taper 235 thus deceases the resistance the implantable tissue retractor faces when it is implanted into the soft tissue of a patient.

In other embodiments, the implantable tissue retractor 200 has a stress-zone taper 240. One area of great stress of the implantable tissue retractor 200 is where the shaft 205 and the retractor member 210 are connected. Failure at this point is undesirable because the retractor member 210 would disconnect and be freely mobile in the hypopharynx of the patient. In some embodiments, the connection between the shaft 205 and the retractor member 210 is strengthened by molding the retractor member 210 and the shaft 205 together as one piece, rather than bonding two separate pieces. In other embodiments, a stress-zone taper 240 is located at the connection between the shaft 205 and the retractor member 210. The stress-zone taper 240 is thickest at the connection between the shaft 205 and the retractor member 210 and decreases in thickness as the stress-zone taper 240 tapers toward the removable coupler 220.

In other embodiments, fillets (not shown) can be design features in the molded part of the connection between the shaft 205 and the retractor member 210 to reduce the sharp transition from the shaft 205 thickness to the retractor head 210. This reduces the stress concentrator at the connection between the shaft 205 and the retractor member 210. In other embodiments, a thin element (not shown) having a high tensile strength (for example, a stainless steel wire) can be molded or over-molded at the connection between the shaft 205 and the retractor member 210.

In other embodiments, the shaft 205 can have an intermediate portion (not shown) located between the first end 215 and the second end 225 of the shaft 205. The first end 215 of the shaft 205 has a first thickness. The intermediate portion has a second thickness. In some embodiments the first thickness is greater than the second thickness. In one embodiment, the intermediate portion (also called the planned failure zone) is located at or near the removable coupler 220. The planned failure zone allows the implantable tissue retractor 200 to separate into two parts if a failure occurs. The two parts can be a small portion of the shaft 205 located near the removable coupler 220 and the retractor member 210 and a larger portion of the shaft 205. The larger portion of the shaft 205 with the retractor member 210 will expel into the pharyngeal area. An advantage of a planned failure zone located at the second end 225 of the shaft 205 is that the first end 215 will take a lot of time to work its way out of the soft tissue of the patient. The movement of the retractor member 210 when the implantable tissue retractor fails, provides ample warning to the patient. The patient is prepared to swallow or spit out the implantable tissue retractor 200 when the implantable tissue retractor 200 is free from the soft tissue of the patient. The failure zone taper can uniformly taper towards the site of the planned failure or the failure zone taper can be abrupt at the site of the planned failure.

In some embodiments, the implantable tissue retractor 200 further comprises an anchor member. In one embodiment the anchor member is about 5 millimeters in length. The anchor member comprises a locking member and a pad. The anchor member is connected to the shaft 205 of the implantable tissue retractor 200 after the implantable tissue retractor 200 has been implanted into the soft tissue of a patient. The anchor member in positioned near the frenulum and functions to keep the implantable tissue retractor 200 in the soft tissue of the patient. In some embodiments the locking member is a crimp lock, a slide lock or a clamshell lock.

Figure 5A:
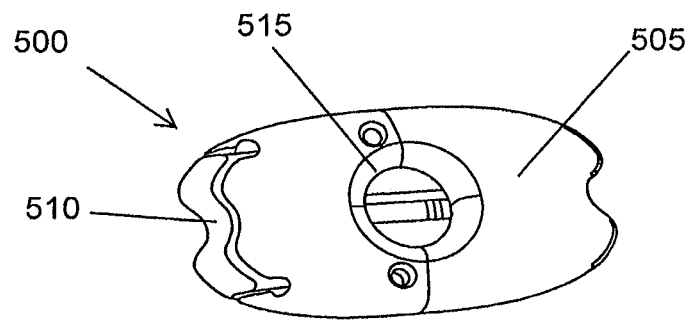
FIG. 5A is a front view of a slide lock in a closed position, according to an illustrative embodiment of the invention.

FIGS. 5A-5G show various positions of a slide lock. FIG. 5A is a front view of a slide lock 500 in a closed position, according to an illustrative embodiment of the invention. In some embodiments, the slide lock 500 is composed of two elements, an outer element 505 and an inner element 510. The outer element 505 serves as a sleeve for the inner element 510 to slide open or closed. In some embodiments, the outer element 505 has an outer aperture 515. The aperture 515 is sized to allow a shaft (for example the shaft 205 of the implantable tissue retractor 200) to pass easily. The inner element 510 can have at least one dimension (for example, height or width) that is smaller than a shaft (for example, the shaft 205 of the implantable tissue retractor 200). The inner element 510 can compress against a shaft and lock the shaft in place. The inner element 510 can slide back to the open position. Sliding the inner element 510 into the open position can release the slide lock 500 and allow the slide lock to be removed or repositioned along a shaft.

Figure 5B:
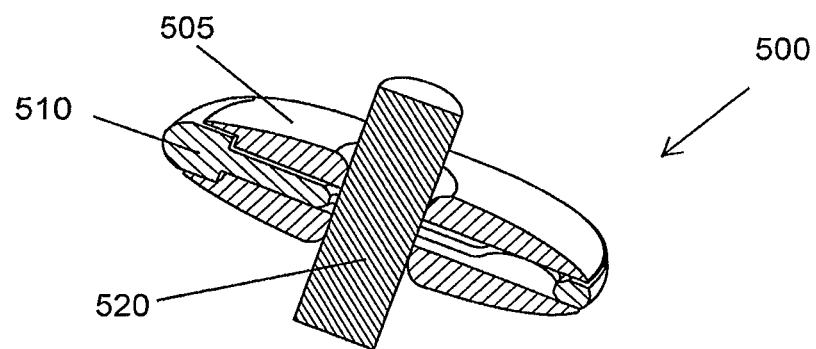
FIG. 5B is a schematic illustration of a cut away of a closed slide lock and shaft, according to an illustrative embodiment of the invention.
Figure 5C:
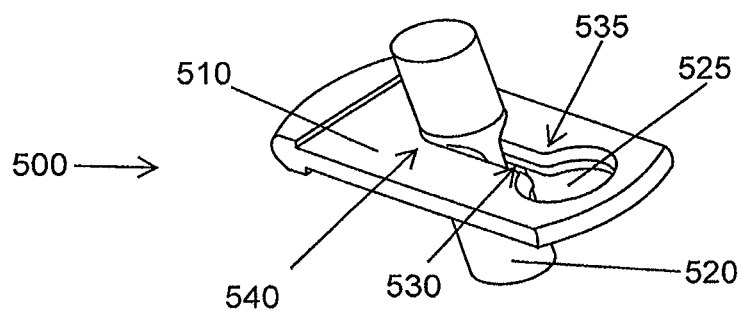
FIG. 5C is a schematic illustration of the inner element of the slide lock and shaft in the closed position, according to an illustrative embodiment of the invention.

FIG. 5B is a schematic illustration of a cut away of a closed slide lock 500 and shaft 520, according to an illustrative embodiment of the invention. The inner element 510 is closed against the shaft 520, locking the shaft 520 in place. FIG. 5C is a schematic illustration of the inner element 510 of a slide lock and shaft 520 in the closed position, according to an illustrative embodiment of the invention. In some embodiments, the inner element 510 comprises an inner aperture 525 and an elongated aperture 530. The shaft 520 enters the inner component 510 through the inner aperture 525. The inner element 510 slides to lock the shaft 520 in the elongated aperture 530. In some embodiments, the elongated aperture 530 is narrower at a first end 535 and wider at a second end 540. This narrowing at the first end 535 prevents the shaft 520 from sliding back into the inner aperture 525.

Figure 5D:
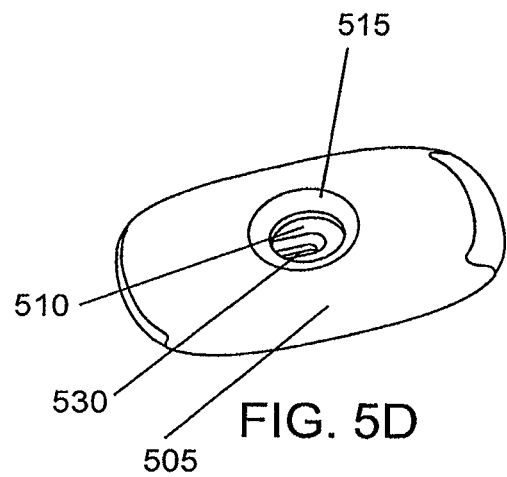
FIG. 5D is a schematic illustration of a slide lock in a closed position, according to an illustrative embodiment of the invention.
Figure 5E:
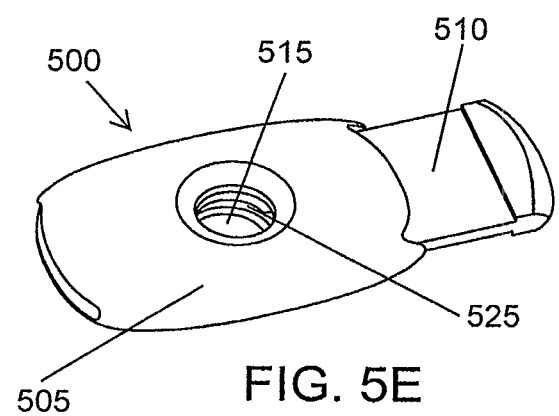
FIG. 5E is a schematic illustration of a slide lock in an open position, according to an illustrative embodiment of the invention.

FIG. 5D is a schematic illustration of a slide lock 500 in a closed position, according to an illustrative embodiment of the invention. In the closed position, the inner element 510 is aligned such that the elongated aperture 530 is aligned with the outer aperture 515 of the outer element 505. FIG. 5E is a schematic illustration of a slide lock 500 in an open position, according to an illustrative embodiment of the invention. In the open position, the inner element 510 is aligned such that the inner aperture 525 is aligned with the outer aperture 515 of the outer element 505.

Figure 5F:
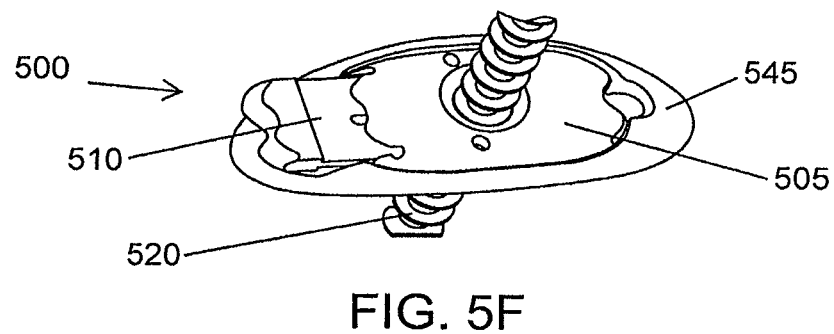
FIG. 5F is a schematic illustration a slide lock in an open position, combined with an anchor pad and mounted on a shaft, according to an illustrative embodiment of the invention.

FIG. 5F is a schematic illustration of a slide lock 500 in an open position, an anchor pad 545 and a shaft 520, according to an illustrative embodiment of the invention. When the slide lock 500 is in the open position, the inner element 510 protrudes from the outer element 505, allowing the outer aperture and the inner aperture to align. The alignment between the inner and outer apertures allows the slide lock to move along the shaft 520. Depending on the direction the slide lock is moving along the shaft 520, the tension of the tissue retractor will increase or decrease.

Figure 5G:
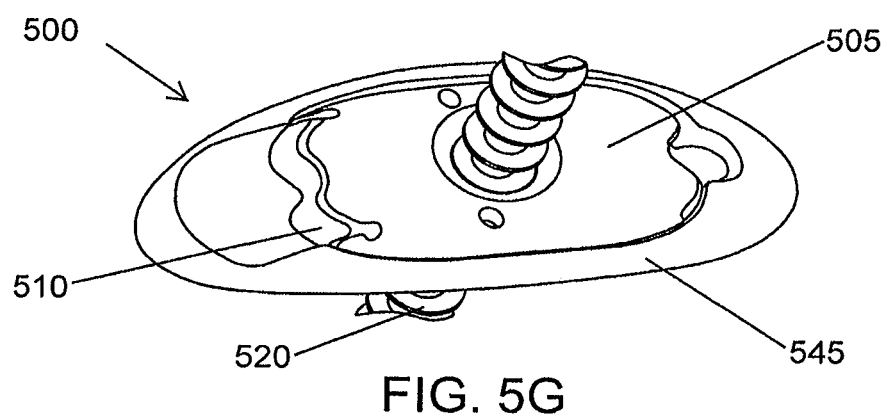
FIG. 5G is a schematic illustration of a slide lock in a closed position, combined with an anchor pad and mounted on a shaft, according to an illustrative embodiment of the invention.

FIG. 5G is a schematic illustration of a slide lock 500 in a closed position, an anchor pad 454 and a shaft 520, according to an illustrative embodiment of the invention. When the slide lock 500 is in the closed position, the inner element 510 no longer protrudes from the outer element (compare FIG. 5F and FIG. 5G). The shaft is locked in place and the tension of the tissue retractor is set.

FIGS. 6A-6H show various embodiments of an anchor pad. FIG. 6A is a schematic illustration of a flat anchor pad 600, according to an illustrative embodiment of the invention. The anchor pad 600 can interface with the soft tissue to distribute counterforce over a large surface area. In some embodiments, the anchor pad does not mechanically couple to the shaft directly. In one embodiment, the anchor pad interfaces with a locking member to obtain counterforce and distributes that counterforce to the soft tissue.

In some embodiments, the anchor pad 600 has a pad aperture 605. The pad aperture 605 is sized to allow a shaft of a tissue retractor to slide through the pad aperture 605. In some embodiments, the anchor pad 600 has a recess 610. The recess 610 is capable of receiving a locking member.

FIG. 6B is a schematic illustration of a curved anchor pad 620, according to an illustrative embodiment of the invention. The curved anchor pad 600 has a pad aperture 605, sized to allow a shaft of a tissue retractor to slide through the pad aperture 605. In some embodiments, the curved anchor pad 620 has a recess 610. The recess 610 allows a locking member to nest in the anchor pad 600.

The shape of the curved anchor pad 620 has many functionalities. The curvature allows the anchor pad to interface with the soft tissue of a patient. In particular, the curvature allows the anchor pad to contact a soft tissue located in the patient's oral cavity or pharynx and distribute a force across the soft tissue, for example the frenulum. In some embodiments the arch of the curve varies depending on the needs of the patient. For example, the arch of the curve can vary to make the pad more comfortable for the patient. The arch of the curve can also be varied to distribute the counterforce to different locations of the soft tissue. Since the frenulum is wedge shaped, the curve of the anchor pad can go down both sides of the wedge-shaped frenulum. In addition, the height of the anchor pad can be minimized since the resting position of the tongue allows minimal space between the tongue and the floor of the mouth. Furthermore, the anchor pad can be made from a flexible material, for example silicon, to conform to the patient by deforming the anchor pad to the patient's contours.

FIG. 6C is a front view of a curved anchor pad 620, according to an illustrative embodiment of the invention. The height between points C1 and C2 is approximately 8 millimeters. In some embodiments, the height between points C1 and C2 is varied depending upon the particular requirements of the patient. For example, the height between points C1 and C2 can be approximately 0.1 millimeters to approximately 20 millimeters.

In some embodiments, the curved anchor pad 620 is made of a translucent or transparent material. Some patients will prefer that the tissue retractor be invisible to the general public. To accomplish this, the curved pad 620 can be made of a translucent or transparent material such as silicon or other translucent, elastic materials. In this embodiment, the patient is not subject to any social stigma about the patient's OSAS because the general public is not aware of the patient's condition.

In other embodiments, the material of the pad is selected based on the need to have the curved pad 620 be made of a rigid material. For example, the curved pad 620 can be made out of stainless steel, titanium, silver, polyacrylic, polycarbonate, nitinol, acrylonitrile butadiene styrene ("ABS") or polytetrafluoroethylene ("PTFE"). In some embodiments, pad is made of a less rigid material. For example, a patient may not be comfortable when an anchor pad is made from a rigid material. Therefore, the anchor pad can be made from an elastic material such as silicon or foam.

FIG. 6D is a top view of a curved anchor pad 620, according to an illustrative embodiment of the invention. The length between points D1 and D2 is approximately 16.5 millimeters. In some embodiments, the length between points D1 and D2 is varied depending upon the particular requirements of the patient. For example, the height between points D1 and D2 can be approximately 1 millimeter to approximately 100 millimeters.

FIG. 6E is a side view of a curved anchor pad 620, according to an illustrative embodiment of the invention. The curved pad 620 can be made from a variety of materials, including silicon and stainless steel. The specific material used to make the curved pad 620 will largely depend on the patient.

FIG. 6F is a perspective view of a curved anchor pad 620, according to an illustrative embodiment of the invention. In some embodiments, the depth of the recess 610 is varied to accommodate varying locking members. The depth of the recess 610 can also be varied for the comfort of the patient to allow a locking member to fully sit within the recess 610, thereby removing potential irritating projections. For example, the depth of the recess can be approximately 0.1 millimeters to approximately 5 millimeters. In some embodiments, the anchor pad does not have a recess to allow for easier access to the locking member.

FIG. 6G is a top perspective view of a curved pad 620, according to an illustrative embodiment of the invention. The height between points G1 and G2 is approximately 8.7 millimeters. In some embodiments, the height between points G1 and G2 is varied depending upon the particular requirements of the patient. For example, the height between points G1 and G2 can be approximately 0.01 millimeters to approximately 10 millimeters. When the anchor pad is flat, the height between points G1 and G2 is zero.

FIG. 6H is a side perspective view of a curved pad 620, according to an illustrative embodiment of the invention. The side 625 can have a variety of shapes. In some embodiments, the side 625 is tapered into a curve 630. In other embodiments, the side 625 is square-shaped or rectangularly-shaped. The shape of the side 625 will largely depend on what is comfortable for a specific patient.

FIGS. 7A-7D show various views of a spherical anchor member. FIG. 7A is a schematic illustration of a spherical anchor member 700 in a halfway closed position. The spherical anchor member 700 comprises an inner element 710 and a spherical element 720. When the spherical anchor member 700 is in a locked position, the inner element 710 is fully enclosed within the spherical element 720, creating a fully spherical shape. When the spherical anchor member 700 is in an open position, the inner element 710 is not fully enclosed within the spherical element 720.

FIG. 7B is a schematic illustration of the inner element 710 of a spherical anchor member, according to an illustrative embodiment of the invention. In some embodiments, the inner element 710 has a stopper 730. When the inner element 710 is inserted into a spherical anchor member, the stopper 730 acts to keep the inner element 710 from inserting too far into a spherical member. In some embodiments, the inner element 710 has an inner aperture 740 sized to allow a shaft of a tissue retractor to slide through the inner aperture 740. In other embodiments, the inner element 710 has an elongated aperture 750. When the spherical anchor member is in a closed position, the elongated aperture 750 engages a shaft of a tissue retractor, locking the tissue retractor in place. In some embodiments, the elongated aperture 750 is narrower at a first end 760 and wider at a second end 770. This narrowing at the first end 760 prevents a shaft of a tissue retractor from sliding back into the inner aperture 740.

FIG. 7C is a schematic illustration of a spherical anchor member 700 in a closed position, according to an illustrative embodiment of the invention. When the spherical anchor member 700 is in the closed position, the inner element 710 no longer protrudes from the outer element (compare FIG. 7A and FIG. 7C). The shaft is locked in place and the tension of the tissue retractor is set.

FIG. 7D is a schematic illustration of a spherical anchor member 700 in an open position, according to an illustrative embodiment of the invention. In some embodiments, the spherical component 720 has an aperture 780. When the aperture 780 of the spherical component 720 is aligned with the inner aperture 740 a shaft can slide through the aligned apertures 780, 740. When the shaft is in the desired position or at a desired tension, the inner element 710 can slide shut, locking the shaft in place.

In some embodiments, the spherical anchor member 700 combines the anchor member and the locking member into one unit. The spherical anchor member 700 tends to be the softest and most comfortable anchor member to a patient, mainly because there are no protrusions from the spherical anchor member 700.

FIG. 8 is a schematic illustration of a tissue retractor 800 according to an illustrative embodiment of the invention. The tissue retractor 800 comprises a shaft 805. The shaft 805 is sized for insertion into a soft tissue located in a patient's oral cavity or pharynx. The shaft 805 has at least one securing feature 810. The tissue retractor 800 also comprises a retractor member 815 connected at or near the first end 820 of the shaft 805. The tissue retractor also comprises an anchor member 825 engagable by at least one securing feature 810. In some embodiments, at least one of the shaft 805, the retractor member 815, or the anchor member 825 is positionable on a surface of the soft tissue. At least one of the shaft 805, the retractor member 805, or the anchor member is adjustable to vary a force that prevents a deformation of at least a portion of the soft tissue to prevent obstruction of a patient's airway.

In some embodiments, the anchor member 825 comprises a locking member 830 and a pad 835. The pad 835 is capable of distributing a force across the soft tissue. In some embodiments, the pad 835 has a recess (not shown). The recess is capable of receiving a locking member.

In some embodiments the securing feature 810 is a protuberance, a cavity, or an aperture (see, e.g., FIGS. 4A-4G). In some embodiments the locking member 830 is a slide lock or a clamshell lock.

In some embodiments the retractor member 815 is a disc shaped, rod shaped, cross-rod shaped, triangularly shaped, saddle shaped, half-saddle shaped, oval shaped or rectangularly shaped (see, e.g., FIGS. 3A-3J).

In some embodiments, the tissue retractor 800 has a first end 820 and a second end 840. The first end 820 has a first thickness. An intermediate portion (not shown) is located between the first end 820 and the second end 840. The intermediate portion has a second thickness. The second thickness is less than the first thickness. Where the first thickness meets the second thickness, a junction (not shown) is formed. In one embodiment, the junction is located at or near the anchor member 825. The junction can be the end of a taper or it can be an abrupt change (e.g., a step change) from the first thickness to the second thickness.

In some embodiments the junction is a planned failure zone. The planned failure zone allows the tissue retractor to break at or near the anchor member. A benefit of this feature is that the patient will be alerted to the fact that the tissue retractor broke when the retractor member starts to the move. The patient will have enough time to either swallow or spit out the tissue retractor as it exits the soft tissue.

In some embodiments, the pad is adapted to be removed from the shaft without removing the locking member from the shaft. In one embodiment, the pad has a slot from the aperture to the outside edge of the pad. If the pad needs to be replaced or if the patient is uncomfortable with that particular pad, a doctor can slide the pad around the shaft using the slot. In some embodiments, a new pad can be slid onto the shaft. The new pad can be more comfortable to the patient. In some embodiments, inserting a new pad can adjust the tension of the tissue retractor. For example, replacing an old pad with a thicker new pad will increase the tension of the tissue retractor. Similarly, replacing an old pad with a thinner new pad will decrease the tension of the tissue retractor.

Figure 9A:
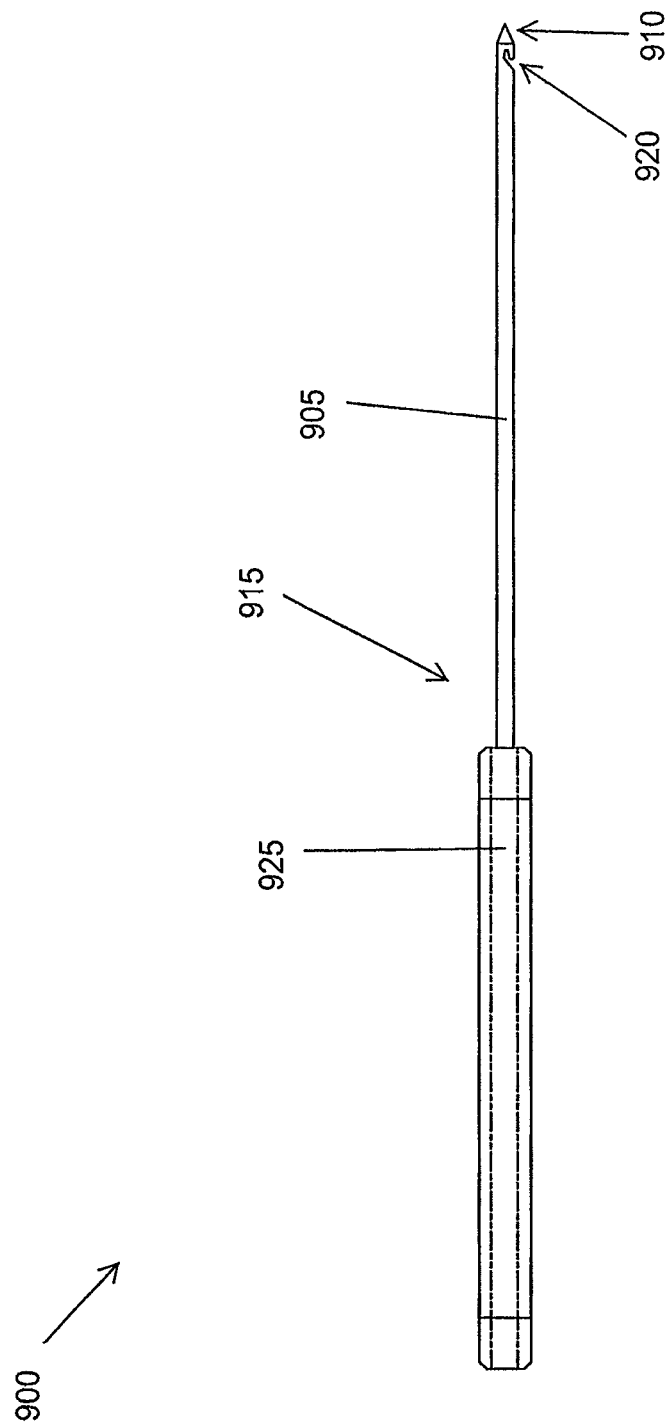
FIG. 9A is a schematic illustration of an implantation device, according to an illustrative embodiment of the invention.

FIG. 9A is a schematic illustration of an implantation device 900, according to an illustrative embodiment of the invention. In some embodiments, the implantation device is used to penetrate the soft tissue of the patient. In one embodiment, the implantation device is used to pull a tissue retractor through the soft tissue of a patient. The implantation device comprises a shaft 905. The shaft 905 has a pointed end 910 and a second end 915. The implantation device 900 also has a first mechanical coupler 920 near the pointed end 910 of the shaft 905. The first mechanical coupler 920 is adapted to couple with a removable coupler of a tissue retractor (not shown). The implantation device 900 also has a handle 925 at the second end 915 of the shaft 905.

Figure 9B:
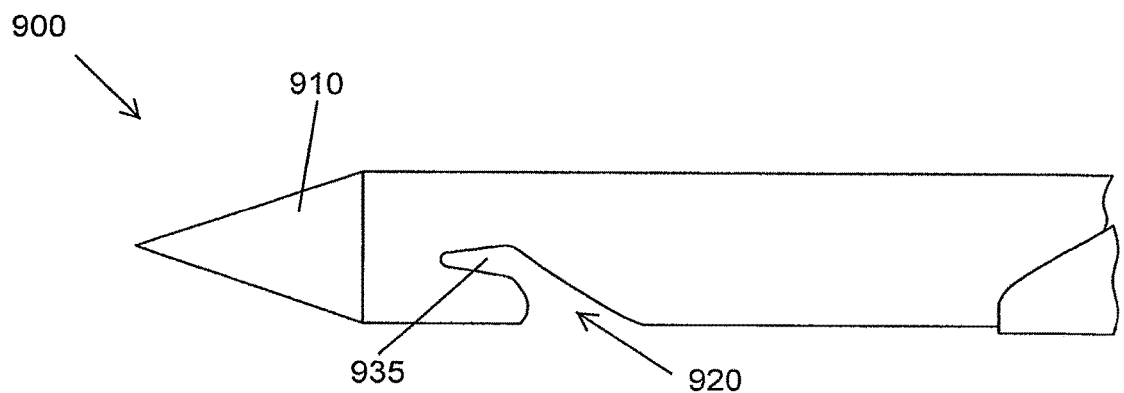
FIG. 9B is a schematic illustration of the pointed end of an implantation device according to an illustrative embodiment of the invention.

FIG. 9B is a schematic illustration of the pointed end 910 of an implantation device 900, according to an illustrative embodiment of the invention. In some embodiments the pointed end of the implantation device is bullet shaped. In one embodiment one or more cutting facets can be added to the pointed end of the implantation device to allow easier passage of the of the implantation device through the soft tissue.

Figure 9C:
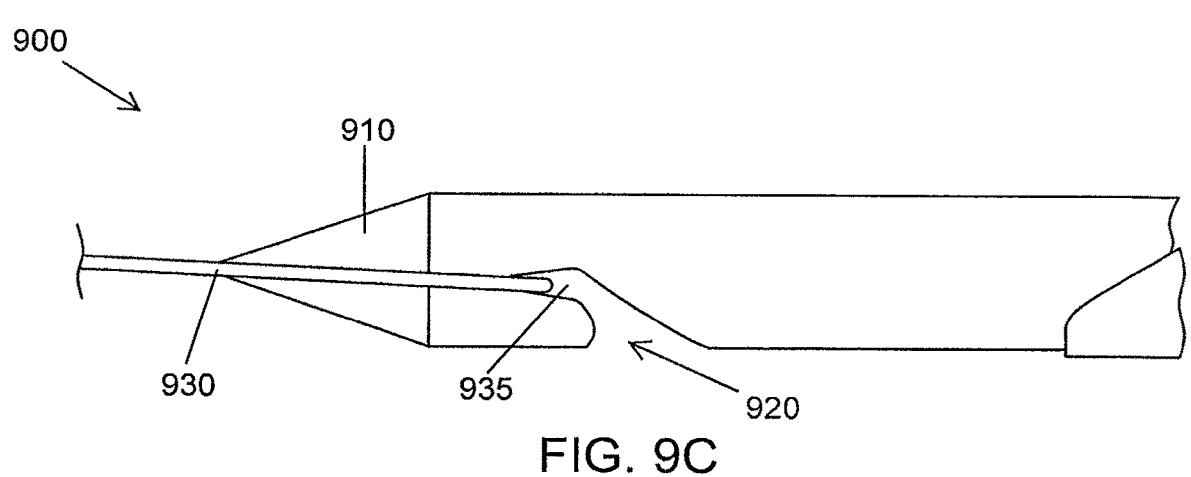
FIG. 9C is a schematic illustration of a mechanical coupler of an implantation device, according to an illustrative embodiment of the invention.

FIG. 9C is a schematic illustration of a mechanical coupler of an implantation device, according to an illustrative embodiment of the invention. In some embodiments, the first mechanical coupler 920 comprises a cleft. The cleft in the implantation device 900 interfaces with a suture loop 930 to capture the suture and allow the tissue retractor to be pulled into the tongue. In inner end 935 of the cleft can narrow to a width slightly thinner than the suture loop 930 diameter to securely lock the suture into the cleft. In another embodiment, the cleft can have depth slightly shorter than the suture loop thickness. The suture loop is slightly compressed and held in place by friction.

In some embodiments the first mechanical coupler (e.g., 920) comprises a suture, a magnet, a vacuum, an adhesive, a screw, or a hook, e.g., in place of the cleft depicted in FIGS. 9A-9E. In some embodiments, the removable coupler of the tissue retractor comprises a suture, a magnet, a vacuum, an adhesive, a screw, or a hook.

Figure 10A:
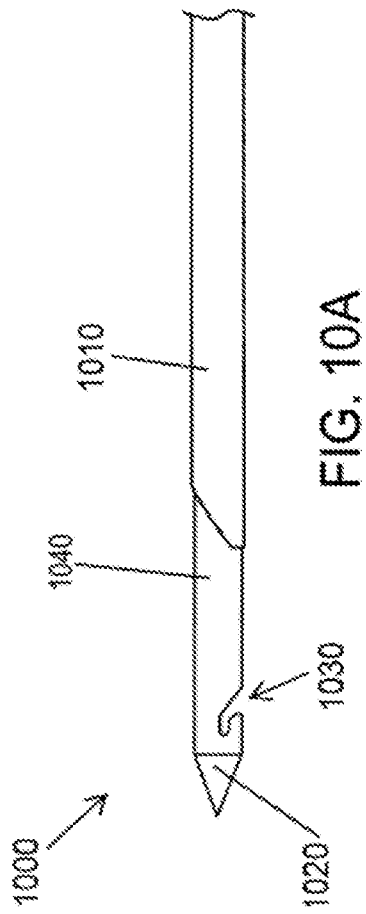
FIG. 10A is a schematic illustration of an implantation device with a releasable locking member in the open position, according to an illustrative embodiment of the invention.

FIG. 10A is a schematic illustration of an implantation device 1000 with a releasable locking member 1010 in the open position, according to an illustrative embodiment of the invention. FIG. 10C is a schematic illustration of an implantation device 1000 with a releasable locking member 1010 in the closed position, according to an illustrative embodiment of the invention. In some embodiments a groove (not shown) runs the length of the implantation device 1000. The groove can contain a rod (not shown) that slides within the groove. A distal end of the rod can be aligned with the opening of the mechanical coupler 1030. A sliding action of the rod within the groove can be used to actuate the mechanical coupler 1030, e.g., between open and closed positions.

In some embodiments, the rod can be in a closed position when the implantation device is inserted through the soft tissue so that the soft tissue is not irritated by the mechanical coupler. When the implantation device penetrates the soft tissue, the rod can slide to an open position, allowing the mechanical coupler to capture the removable coupler of the implantable tissue retractor. The rod can then slide back to a closed position as the implantation device is withdrawn through the soft tissue, thereby implanting the implantable tissue retractor.

In some embodiments, when the rod is sliding back and forth along the implantation device, the rod is accessible to a surgeon. In one embodiment, a protuberance on the rod allows the doctor to push the rod forward or backwards by manipulating the rod with one or more fingers. In other embodiments, other control mechanisms, for example a handle with a trigger interfacing with the rod, are used.

In another embodiment, the releasable locking member 1010 is a sheath. In this embodiment, the implantation device is partially or fully surrounded by a sheath. The sheath can fit over the implantation device like a tube and can slide along the implantation device. In one embodiment, the sheath is advanced to cover the mechanical coupler 1030 to lock a removable coupler of a tissue retractor in place (FIG. 10C). In another embodiment, the sheath is advanced further up the implantation device to cover the pointed end 1020 of the shaft 1040 thus preventing the pointed end 1020 from accidently penetrating the soft tissue.

Figure 10B:
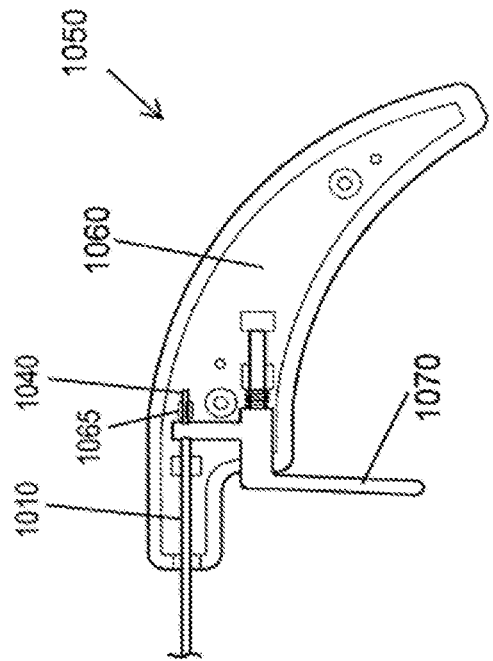
FIG. 10B is a schematic illustration of a releasable locking member control mechanism in the open position, according to an illustrative embodiment of the invention.
Figure 10C:
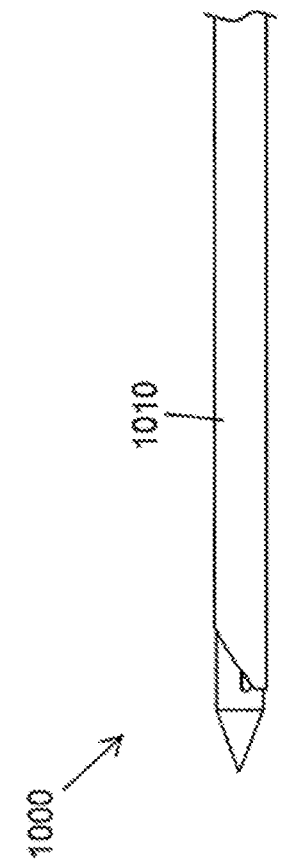
FIG. 10C is a schematic illustration of an implantation device with a releasable locking member in the closed position, according to an illustrative embodiment of the invention.
Figure 10D:
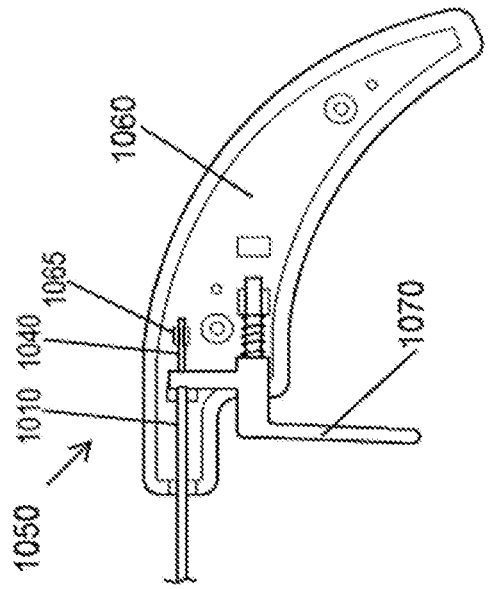
FIG. 10D is a schematic illustration of a releasable locking member control mechanism in the closed position, according to an illustrative embodiment of the invention.

FIG. 10B is a schematic illustration of a releasable locking member control mechanism 1050 in the open position, according to an illustrative embodiment of the invention. FIG. 10D is a schematic illustration of a releasable locking member control mechanism 1050 in the closed position, according to an illustrative embodiment of the invention. In some embodiments the releasable locking member control mechanism 1050 is contained within a handle 1060 of the implantation device. In one embodiment, the handle 1060 is curved. In some embodiments, a doctor can manipulate a bar 1070 to move the releasable locking member to an open position (FIGS. 10A and 10B) or to a closed position (FIGS. 10C and 10D). In some embodiments, the sheath is configured to hinder an unintentional disengagement of a removable coupler of an implantable tissue retractor.

In some embodiments, the handle 1060 contains a tension 1065. The tension meter 1065 is capable of measuring the tension of a shaft of an implantable tissue retractor. In some embodiments, the tension meter 1065 is a spring tension meter, a belt tension meter, a mechanical tension meter, or a tension sensor.

Figure 11:
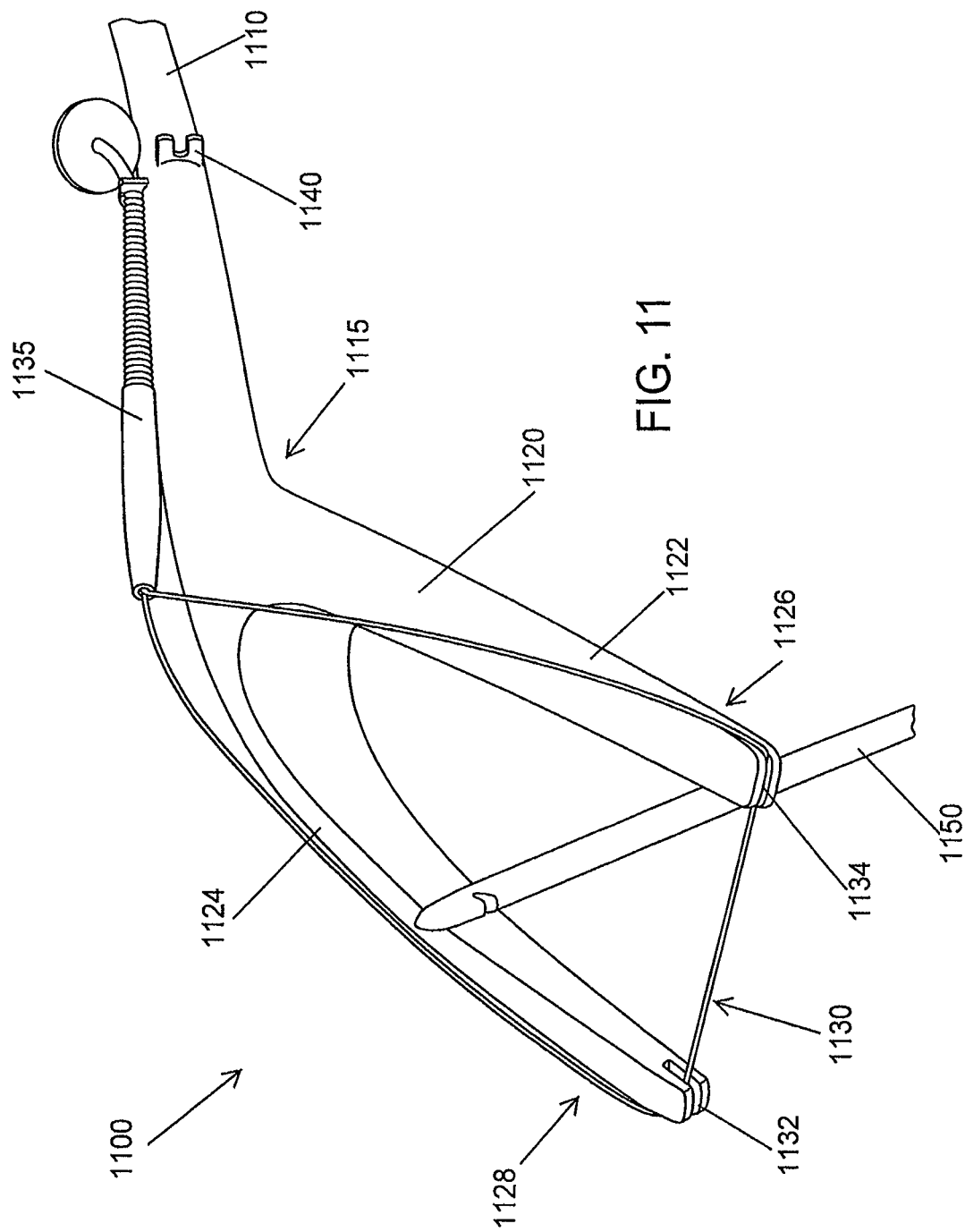
FIG. 11 is a schematic illustration of a tissue retractor holder, according to an illustrative embodiment of the invention.

FIG. 11 is a schematic illustration of a tissue retractor holder 1100, according to an illustrative embodiment of the invention. The tissue retractor holder 1100 comprises a handle 1110. The tissue retractor holder 1100 also comprises a retainer 1120 disposed at a distal end 1115 of the handle 1110. The retainer 1120 releasably retains a removable coupler 1130 of an implantable tissue retractor 1135. The tissue retractor holder 1100 also comprises a detainer 1140. The detainer 1140 is positioned along the handle 1110. The detainer 1140 releasably engages an implantable tissue retractor 1135. The retainer 1120 is adapted to provide a force to a soft tissue of a patient's oral cavity. The force prevents deformation of the soft tissue when an implantation device 1150 is inserted into an opposite side of a soft tissue.

In some embodiments, the retainer 1120 comprises a first forked arm 1122 and a second forked arm 1124. The first and second forked arms 1122, 1124 can extend from the distal end 1115 of the handle 1110. In one embodiment, the distal end 1126 of the first forked arm 1122 is connected to the distal end 1128 of the second forked arm 1124 forming a continuous surface. In some embodiments, the tissue retractor holder 1100 is curved where the handle 1110 joins the retainer 1120 to allow the tissue retractor holder 1100 to reach beyond a tongue base curve.

In some embodiments, the distal end 1126 of the first forked arm 1122 and the distal end 128 of the second forked arm 1124 contain grooves 1132, 1134. The grooves 1132, 1134 can engage a removable coupler 1130 of the implantable tissue retractor 1135.

In some embodiments, the detainer 1140 comprises at least one of a groove, a clamp or a clip. FIG. 11 depicts the detainer 1140 as a clip that is located along the top and sides of the tissue retractor holder 1100. The detainer 1140 can be located along the top, bottom, or sides of the handle 1110 of the tissue retractor holder 1100. In some embodiments, the handle 1110 of the tissue retractor holder 1100 can contain more than one detainer 1140. In one embodiment, the detainer 1140 detains more than one implantable tissue retractor 1135. In some embodiments a surgeon removes the implantable tissue retractor 1135 from the detainer 1140 by using his/her fingers.

The detainer 1140 is used to detain an implantable tissue retractor 1135. In some embodiments, a surgeon can manually insert the implantable tissue retractor 1135 and connect the removable coupler of the implantable tissue retractor 1135 with the mechanical coupler of the implantation device. However, there is very little room within the oral cavity for the surgeon to work. In addition, when the surgeon places his/her fingers into the oral cavity, the surgeon can block his/her view of the mechanical coupler of the implantation device. Moreover, the oral cavity is wet due to the patient's saliva and the surgeon may not be able to maintain a proper grip on the implantable tissue retractor once the implantable tissue retractor is inserted into the oral cavity. Therefore, the detainer 1140 is used to detain an implantable tissue retractor. The detainer allows the implantable tissue retractor to be inserted into the oral cavity of the patient while providing the surgeon with an improved view of the mechanical coupler of the implantation device. The surgeon can effectively perform the procedure while maintaining full sight of the patient's oral cavity and maintaining a proper grip on the implantable tissue retractor.

Figure 12:
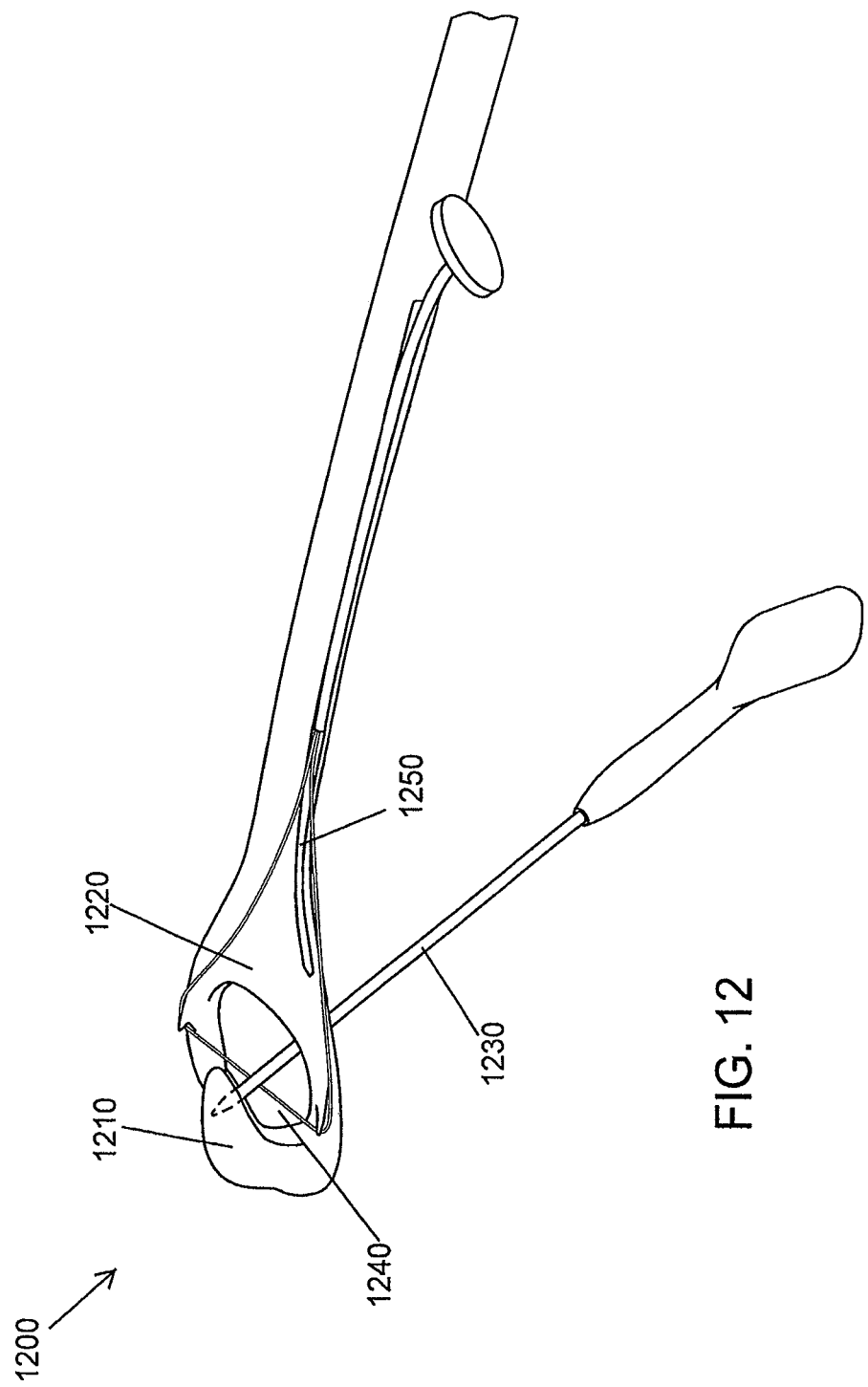
FIG. 12 is a schematic illustration of a guard of a tissue retractor holder, according to an illustrative embodiment of the invention.

FIG. 12 is a schematic illustration of a guard 1210 of a tissue retractor holder 1200, according to an illustrative embodiment of the invention. The guard 1210 is disposed at or near the retainer 1220. The guard 1210 is configured to impede an excessive progression of an implantation device 1230 during implantation of a tissue retractor, thereby protecting the soft tissue from inadvertent puncture. In some embodiments, the guard has a visor 1240. The visor 1240 is an opening that allows the surgeon to see the implantation device 1230. It is preferable that the guard 1210 does not block the surgeon's view of the implantation device 1230. FIG. 12 depicts the detainer 1250 as a groove that is located along the bottom of the tissue retractor holder 1200.

One aspect of the invention features a kit for the treatment of a breathing disorder. The kit comprises an implantable tissue retractor and a tissue retractor holder. The implantable tissue retractor comprises a shaft sized for insertion into a soft tissue located in a patient's oral cavity or pharynx. The tissue retractor also comprises a retractor member disposed at or near a first end of the shaft. The tissue retractor also comprises a removable coupler connected at or near a second end of the shaft.

The tissue retractor holder comprises a handle and a retention system disposed at a distal end of the handle. The retention system temporarily retains a removable coupler. The tissue retractor holder also comprises a detainer positioned on the handle. The detainer is capable of engaging the implantable tissue retractor.

In some embodiments, the kit also contains an implantation device. The implantation device comprises a shaft having a pointed end and a second end. The implantation device also has a mechanical coupler near the pointed end of the shaft. The mechanical coupler is adapted to couple with the removable coupler. The implantation device also has a handle at the second end.

FIGS. 13-24 depict exemplary methods for the treatment of OSAS. The invention relates to a reverse threading method for securing an implantable tissue retractor within the soft tissue of a patient. The method can occur in a doctor's office under local anesthesia and has minimal post procedural discomfort.

Figure 13:
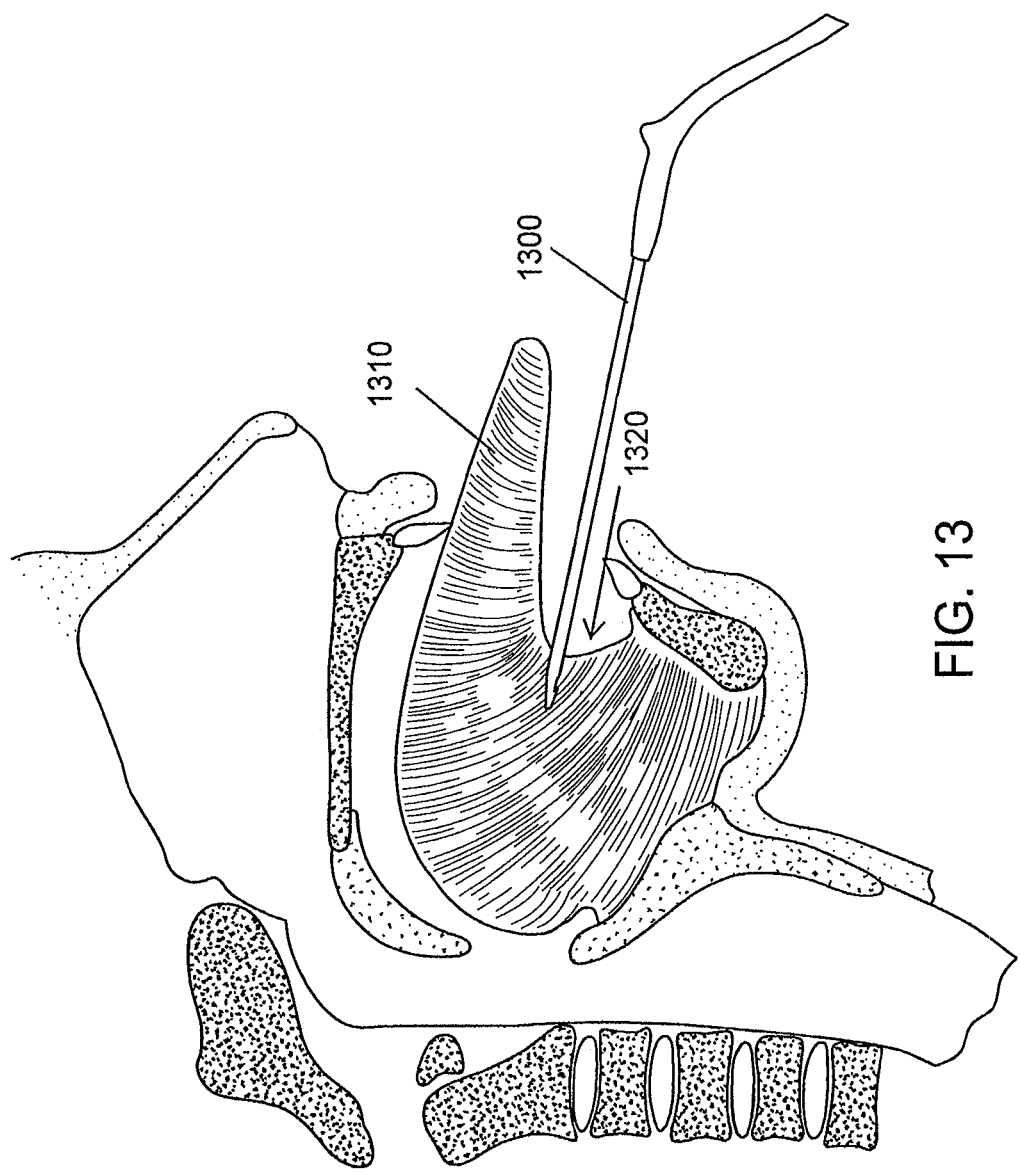
FIG. 13 is a schematic illustration of an insertion of an implantation device, according to an illustrative embodiment of the invention.

FIG. 13 is a schematic illustration of an insertion of an implantation device 1300, according to an illustrative embodiment of the invention. In some embodiments the tongue 1310 is raised to expose the undersurface 1320 of the tongue 1310. In one embodiment, the implantation device 1300 is inserted into the midline, corresponding to the edge of the frenulum of the tongue 1310. In another embodiment, the implantation device 1300 is inserted above the frenulum into the undersurface 1320 of the tongue 1310.

In some embodiments, after the implantation device 1300 is inserted, the tongue 1310 is kept straight as the implantation device 1300 advances though the tongue 1310. A straight tongue allows the implantation device 1300 to penetrate the tongue 1310 at a proper depth and within the tongue's midline. In some embodiments, to confirm a desired position, the implantation device 1300 is palpated within the tongue 1310. In one embodiment, the implantation device 1300 is angled superiorly to form a bulge of the superior tongue surface.

Figure 14:
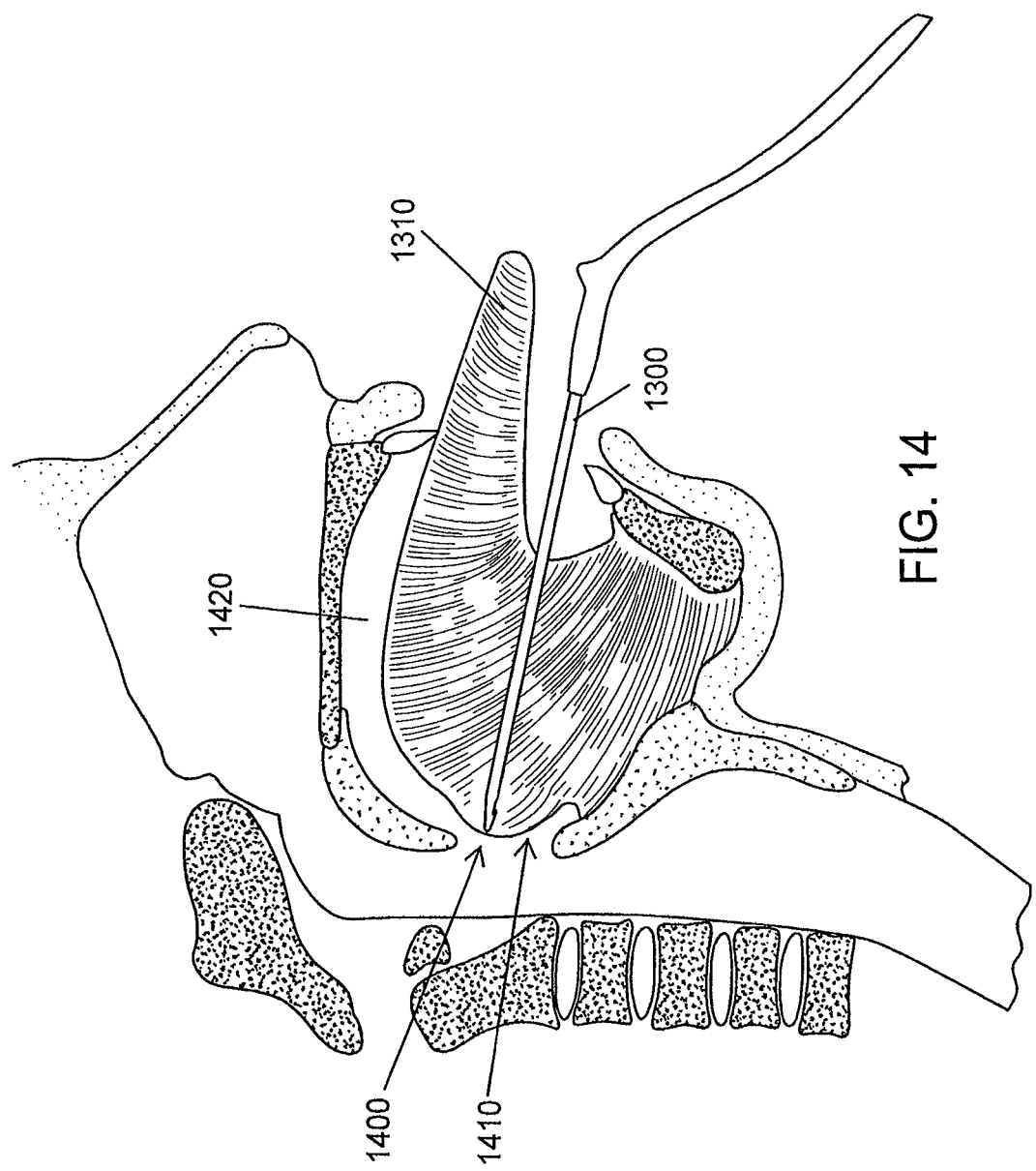
FIG. 14 is a schematic illustration of a tenting up of a soft tissue as the implantation device pushes against the soft tissue, according to an illustrative embodiment of the invention.

FIG. 14 is a schematic illustration of a tenting up 1400 of a soft tissue as the implantation device 1300 pushes against the soft tissue, according to an illustrative embodiment of the invention. In some embodiments, when the implantation device 1300 reaches the tongue base mucosa 1410, the tongue 1310 is retracted downward to provide maximum exposure for the doctor. The tongue base mucosa 1410 can have more connective tissue than the inside of the tongue 1310 and therefore the tongue base mucosa 1410 can resist penetration by the implantation device 1300 causing the tongue base mucosa 1410 to tent up 1400.

Figure 15:
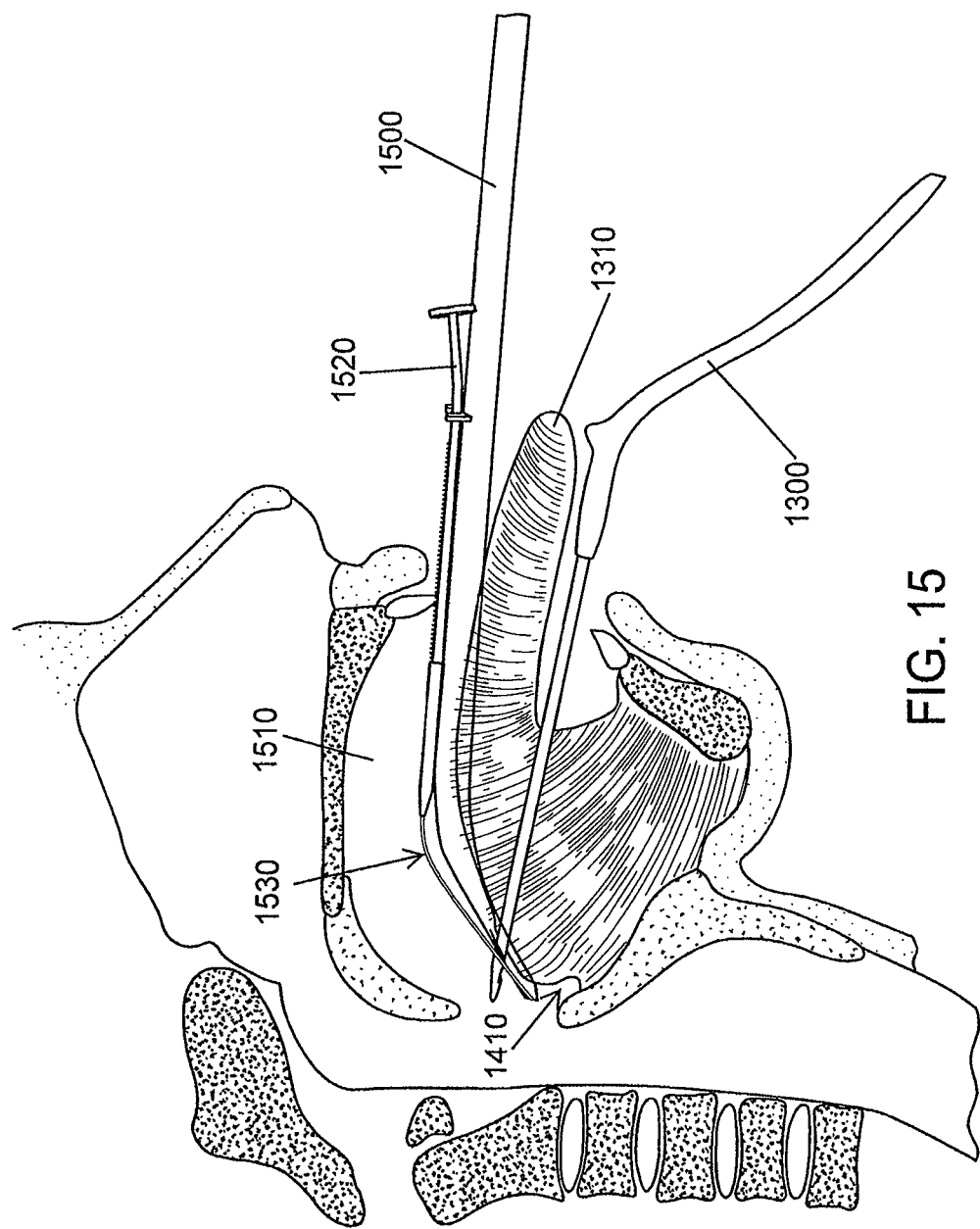
FIG. 15 is a schematic illustration of the tissue retractor holder providing counter pressure, according to an illustrative embodiment of the invention.

FIG. 15 is a schematic illustration of the tissue retractor holder 1500 providing counter pressure, according to an illustrative embodiment of the invention. In some embodiments, to prevent the tongue base mucosa 1410 from tenting up 1400, a counterforce is applied to the area of the tongue 1310 where the implantation device 1300 exits. In one embodiment, the counterforce is applied by a tissue retractor holder 1500.

In some embodiments, the tissue retractor holder 1500 depresses the tongue 1310 providing more oral cavity space 1510 for the surgeon. Referring to FIG. 14, the oral cavity space 1420 is minimal providing little room for the surgeon to work. Referring to FIG. 15, the oral cavity space 1510 is larger when the tissue retractor holder 1500 is used to depress the tongue 1310 than the oral cavity space 1420 when the tissue retractor holder 1500 is not used to depress the tongue 1310.

In some embodiments, the tissue retractor holder 1500 holds the implantable tissue retractor 1520. In one embodiment, the tissue retractor holder 1500 positions the removable coupler 1530 so that it can easily be engaged by a mechanical coupler of the implantation device 1300.

Figure 16:
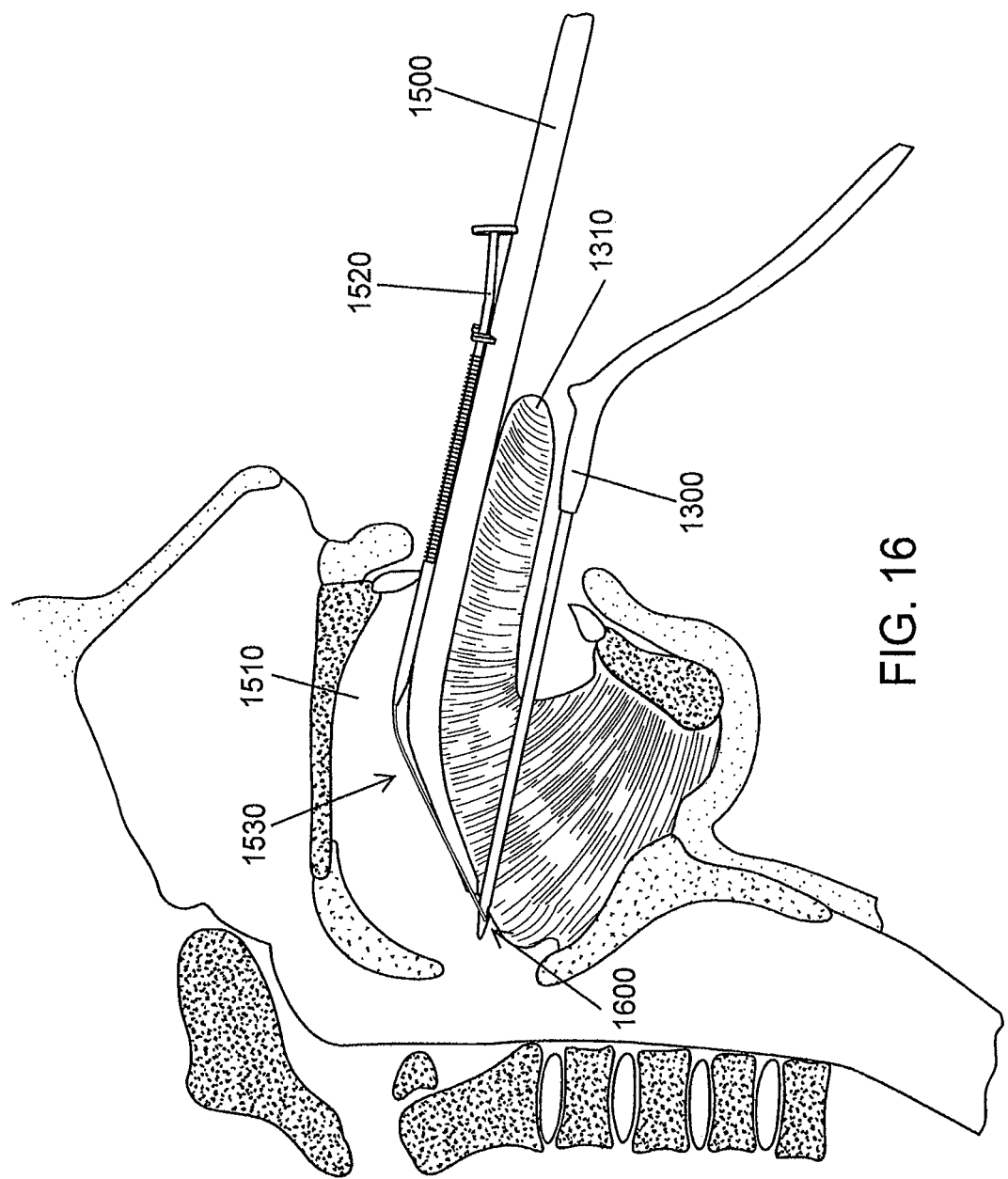
FIG. 16 is a schematic illustration of a mechanical coupler of an implantation device engaging a removable coupler of an implantable tissue retractor, according to an illustrative embodiment of the invention.

FIG. 16 is a schematic illustration of a mechanical coupler 1600 of an implantation device 1300 engaging a removable coupler 1530 of an implantable tissue retractor 1520, according to an illustrative embodiment of the invention. The mechanical coupler 1600 of the implantation device 1300 is coupled to the removable coupler 1530 of the implantable tissue retractor 1520.

In one embodiment, the removable coupler 1610 comprises a suture and the mechanical coupler 1600 comprises a cleft. In this embodiment, the suture is positioned in the cleft. In some embodiments the cleft is located toward the tip of the implantation device 1300 so the implantation device 1300 does not penetrate too far into the oral cavity 1510. In one embodiment, the cleft is oriented at an optimum position so the suture is positioned deep into the cleft when the implantation device 1300 is removed.

In some embodiments, the tissue retractor holder 1500 is pulled slightly backward to engage the mechanical coupler 1600. In one embodiment where the removable coupler 1530 is a suture, when the tissue retractor holder 1500 is pulled backward the surgeon can feel the tension created when the suture is pulled against the implantation device 1300. The surgeon can then slowly pull the implantation device out of the tongue 1310 under the surgeon feels the mechanical coupler 1600 engage the removable coupler 1530.

Figure 17:
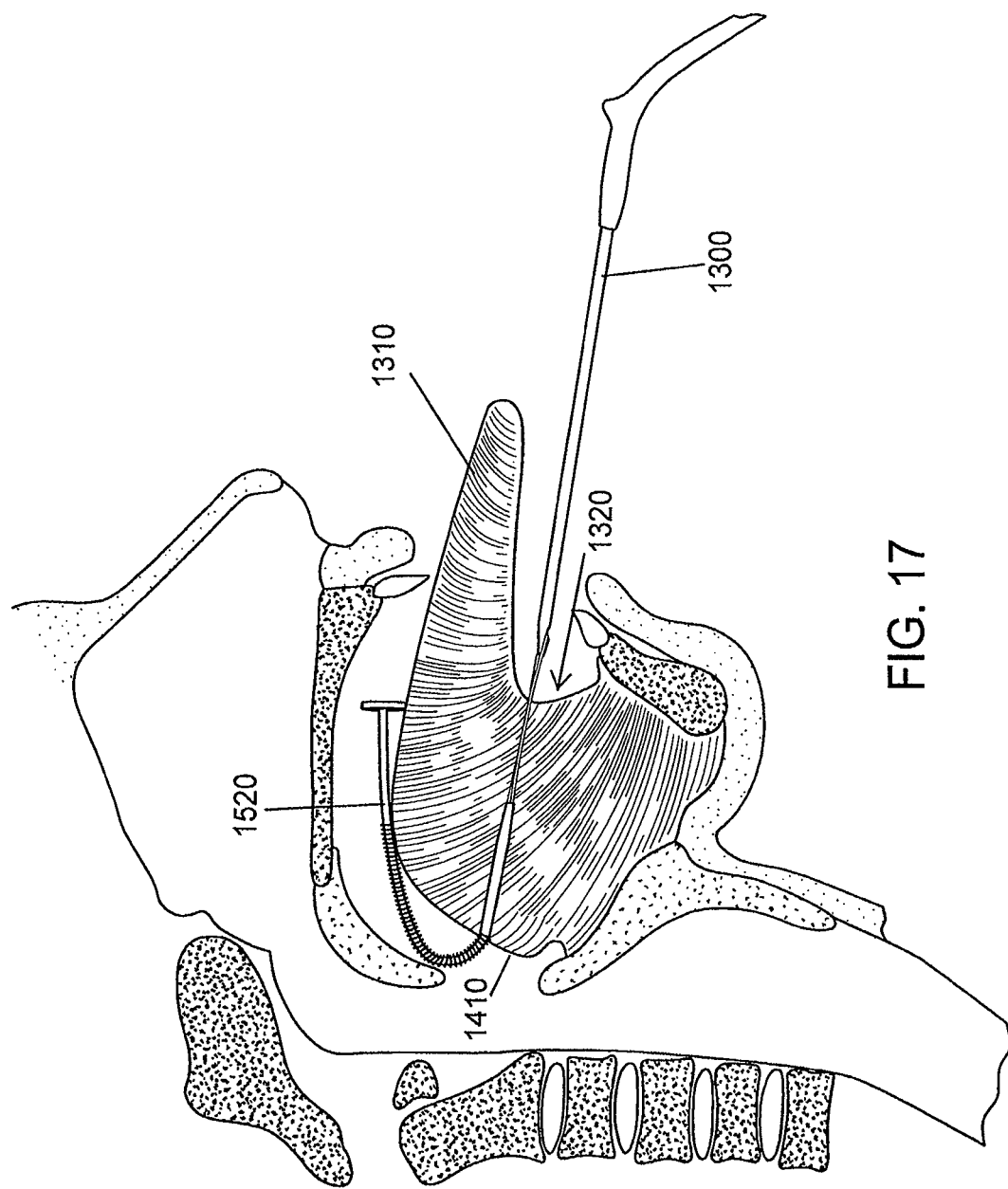
FIG. 17 is a schematic illustration of an implantation device pulling an implantable tissue retractor into a soft tissue, according to an illustrative embodiment of the invention.

FIG. 17 is a schematic illustration of an implantation device 1300 pulling an implantable tissue retractor 1520 into a soft tissue, according to an illustrative embodiment of the invention. In some embodiments, as the implantation device 1300 is withdrawn from the tongue 1310, the implantable tissue retraction 1520 is pulled from the tongue base mucosa 1410, through the tongue 1310, and out the underside 1320 of the tongue 1310.

In some embodiments, the implantable tissue retractor 1520 is made from a flexible material, for example silicon, so that the implantable tissue retractor can bend along the curve of the tongue 1310.

In some embodiments, the implantation device comprises an anchor member. After the implantable tissue retractor is secured within the tongue and before the implantation device is disengaged from the implantable tissue retractor, the anchor member is slid from the implantation device onto the implantable tissue retractor. In one embodiment, the anchor member comprises a locking member and a pad. In this embodiment, the implantation device comprises both the locking member and the pad and both the locking member and the pad are slid from the implantation device to the implantable tissue retractor.

Figure 18:
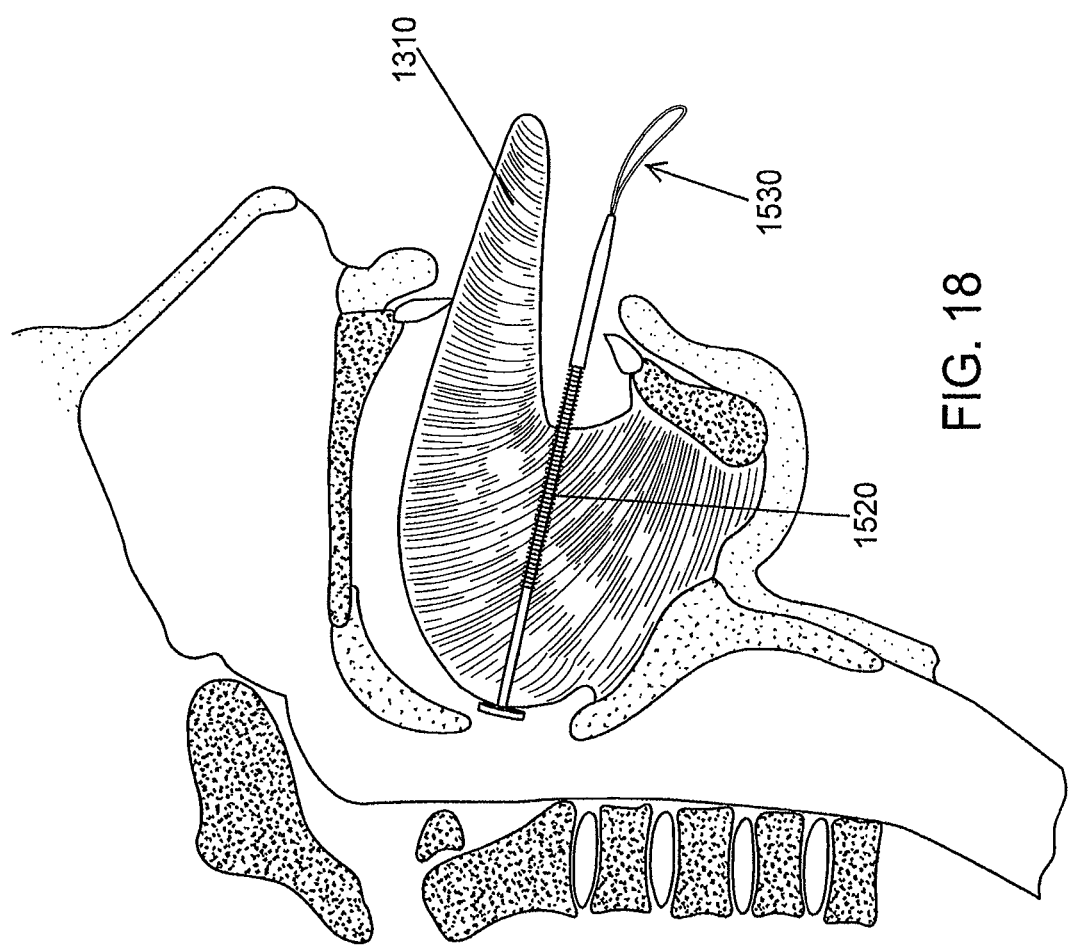
FIG. 18 is a schematic illustration of an implantable tissue retractor in a soft tissue, according to an illustrative embodiment of the invention.

FIG. 18 is a schematic illustration of an implantable tissue retractor 1520 in a soft tissue, according to an illustrative embodiment of the invention. In some embodiments, the implantation device (not shown) is removed from the implantable tissue retractor 1520 after the implantable tissue retractor 1520 is secured within the tongue 1310. The end of the implantable tissue retractor 1520, including the removable coupler 1530, protrude beneath the tongue 1310 and in some embodiments protrude out of the mouth.

Figure 19:
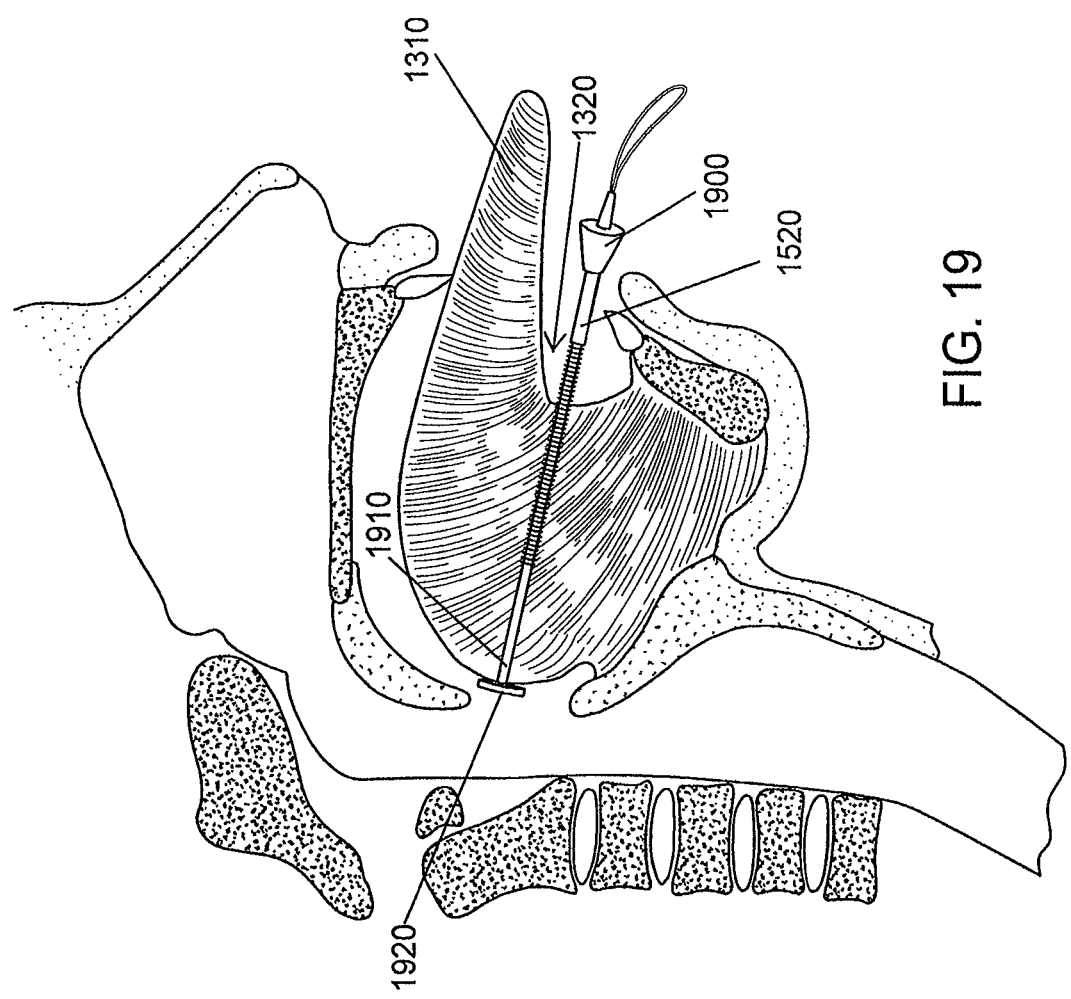
FIG. 19 is a schematic illustration of an anchor member being placed on a shaft, according to an illustrative embodiment of the invention.

FIG. 19 is a schematic illustration of an anchor member 1900 being placed on a shaft 1910, according to an illustrative embodiment of the invention. In some embodiments, after the implantation device (not shown) has been disengaged from the removable coupler, an anchor member 1900 is threaded onto the shaft 1910 and secured to the implantable tissue retractor 1520. The anchor member 1900 provides a counterforce against the undersurface 1320 of the tongue 1310. The counterforce is transmitted through the shaft 1910 to the retractor member 1920.

Figure 20:
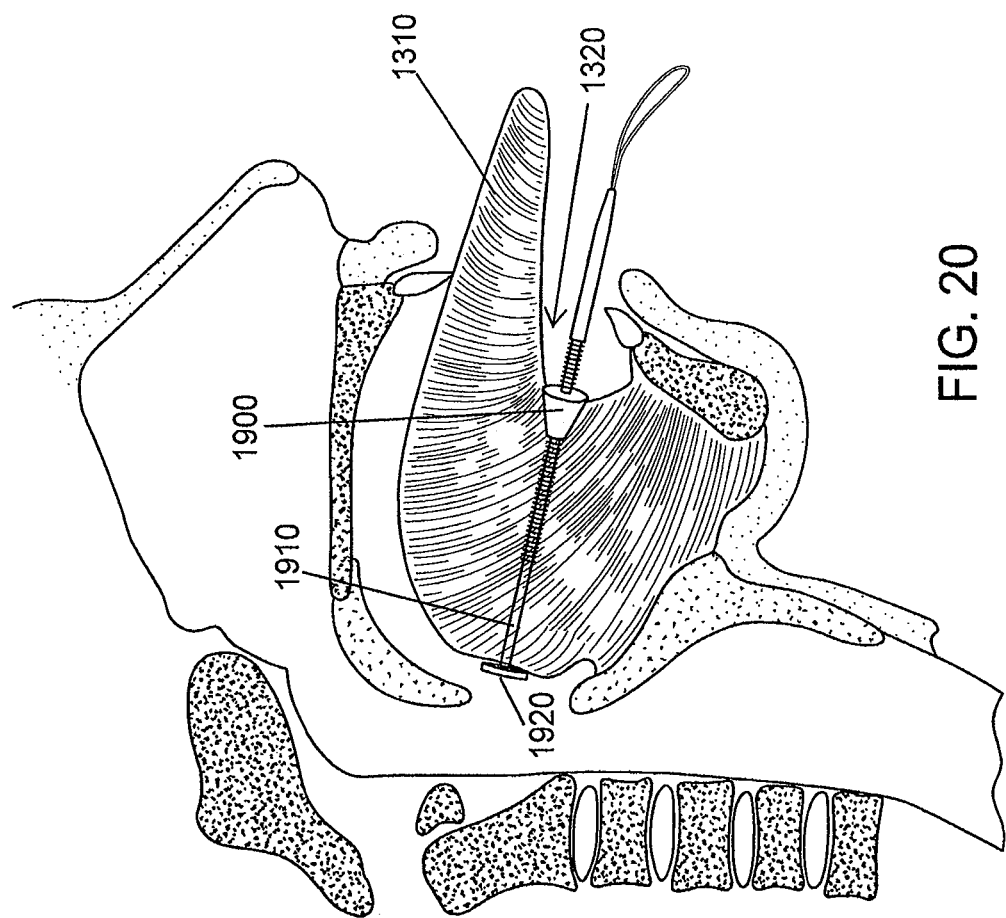
FIG. 20 is a schematic illustration of an anchor member in place on a shaft, according to an illustrative embodiment of the invention.

FIG. 20 is a schematic illustration of an anchor member 1900 in place on a shaft 1910, according to an illustrative embodiment of the invention. In some embodiments, a portion of the anchor member 1900 sinks into the undersurface 1320 of the tongue 1310. In one embodiment, the entire anchor member 1900 sinks into the undersurface 1320 of the tongue 1310.

In some embodiments, the tension from the anchor member 1900 causes the retractor member 1920 to create a concavity in the tongue base mucosa. This concavity is desirable because it prevents the soft tissue from collapsing into the oral cavity and causing OSAS.

Figure 21:
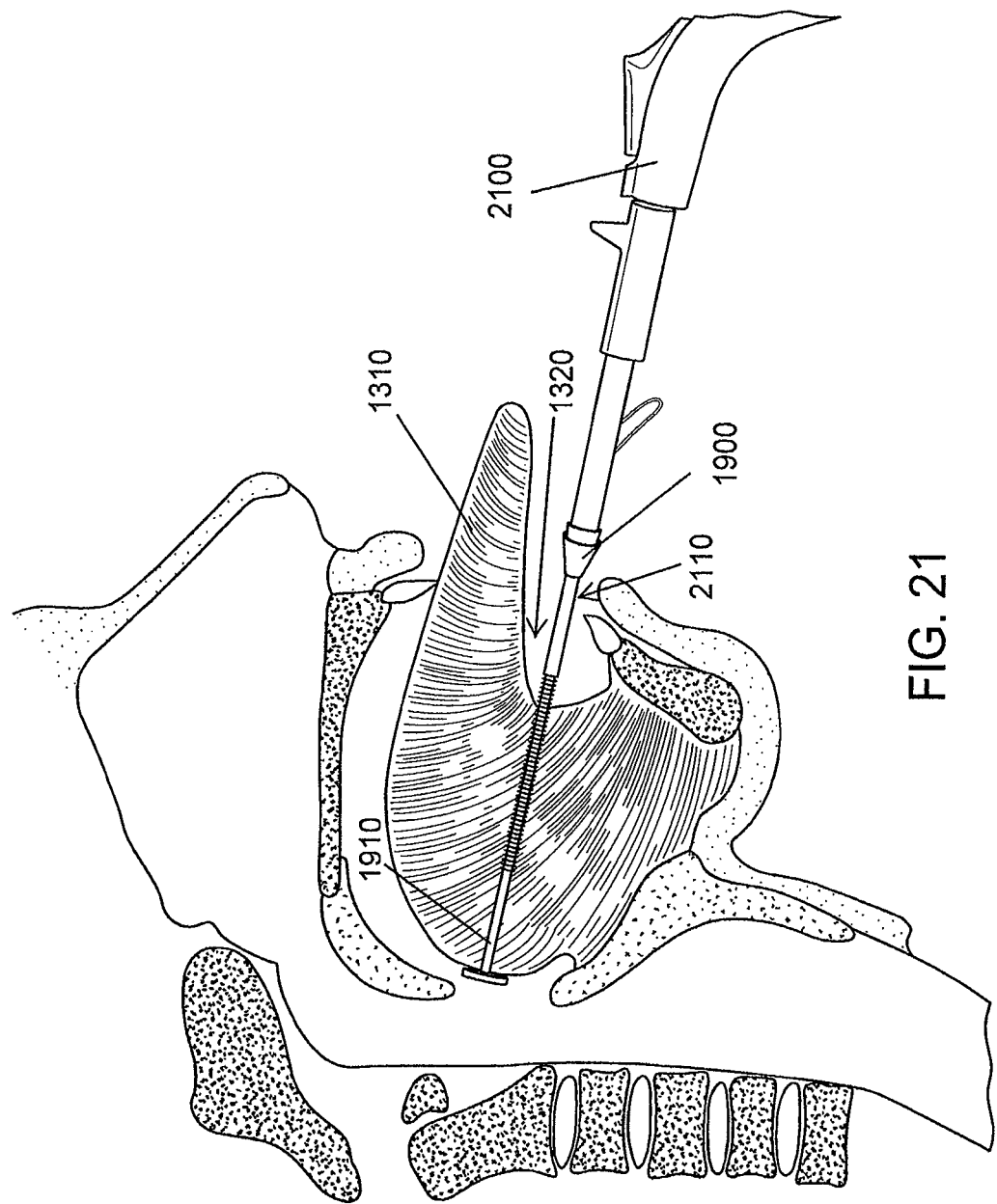
FIG. 21 is a schematic illustration of positioning an anchor member on a shaft using a locking and tensioning tool, according to an illustrative embodiment of the invention.

FIG. 21 is a schematic illustration of positioning an anchor member 1900 on a shaft 1910 using a locking and tensioning tool 2100, according to an illustrative embodiment of the invention. In some embodiments, a securing force can be established by pulling the distal end 2110 of the shaft 1910 with a tension meter. In one embodiment, the tension meter is located within the locking an tensioning tool 2100. As the anchor member 1900 is snug against the underside 1320 of the tongue 1310, the anchor member 1900 can be locked in place when the shaft 1910 is measured to be at a sufficient tension. After the anchor member 1900 is locked in place, the remainder of the shaft 1910 that is protruding from the underside 1320 of the tongue 1310 is removed.

The amount of securing force needed to prevent OSAS varies depending on the individual. In some embodiments, the securing force is between about zero to about 1000 grams. In some embodiments, the securing force is between about 5 to about 200 grams. In some embodiments, the securing force is between about 10 to about 75 grams. In one embodiment, the securing force is about 25 grams.

Figure 22:
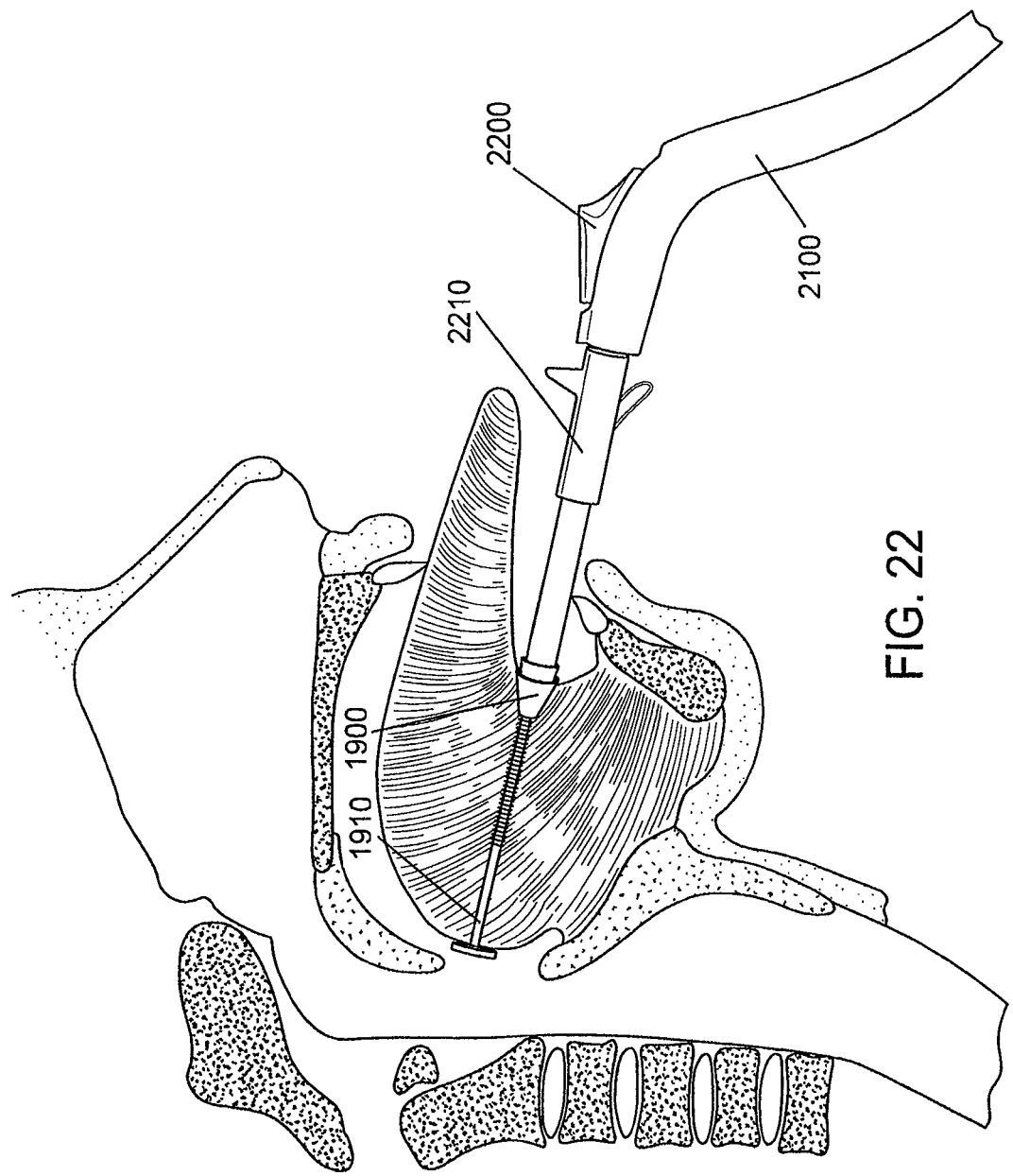
FIG. 22 is a schematic illustration of setting the tension and locking the anchor member in place on a shaft, according to an illustrative embodiment of the invention.

FIG. 22 is a schematic illustration of setting the tension and locking the anchor member 1900 in place on a shaft 1910, according to an illustrative embodiment of the invention. In some embodiments, a locking and tensioning tool 2100 is used to hold the anchor member 1900 for positioning along the shaft 1910. In one embodiment, the locking and tensioning tool 2100 is capable of locking and unlocking the anchor member 1900. In some embodiments, the locking and tensioning tool 2100 has a thumb lock 2200. A doctor can use the thumb lock 2200 to lock and unlock the anchor member 1900. For example, when the doctor pushes the thumb lock 2200 forward, the locking mechanism 2210 is in the back position and the anchor member 1900 is locked.

In some embodiments, the amount of securing force is established by adjusting the length of the shaft. For example, shortening the shaft of the implantable tissue retractor results in a greater tension. Lengthening the shaft of the implantable tissue retractor results in less tension. In some embodiments, the amount of securing force is adjusted by adjusting a physical characteristic of the shaft of the implantable tissue retractor. For example, the shaft could be made of a material that has a higher elasticity, thereby decreasing the amount of force applied to the soft tissue or the shaft could be made of a material with a lower elasticity, thereby increasing the amount of force applied to the soft tissue.

Figure 23:
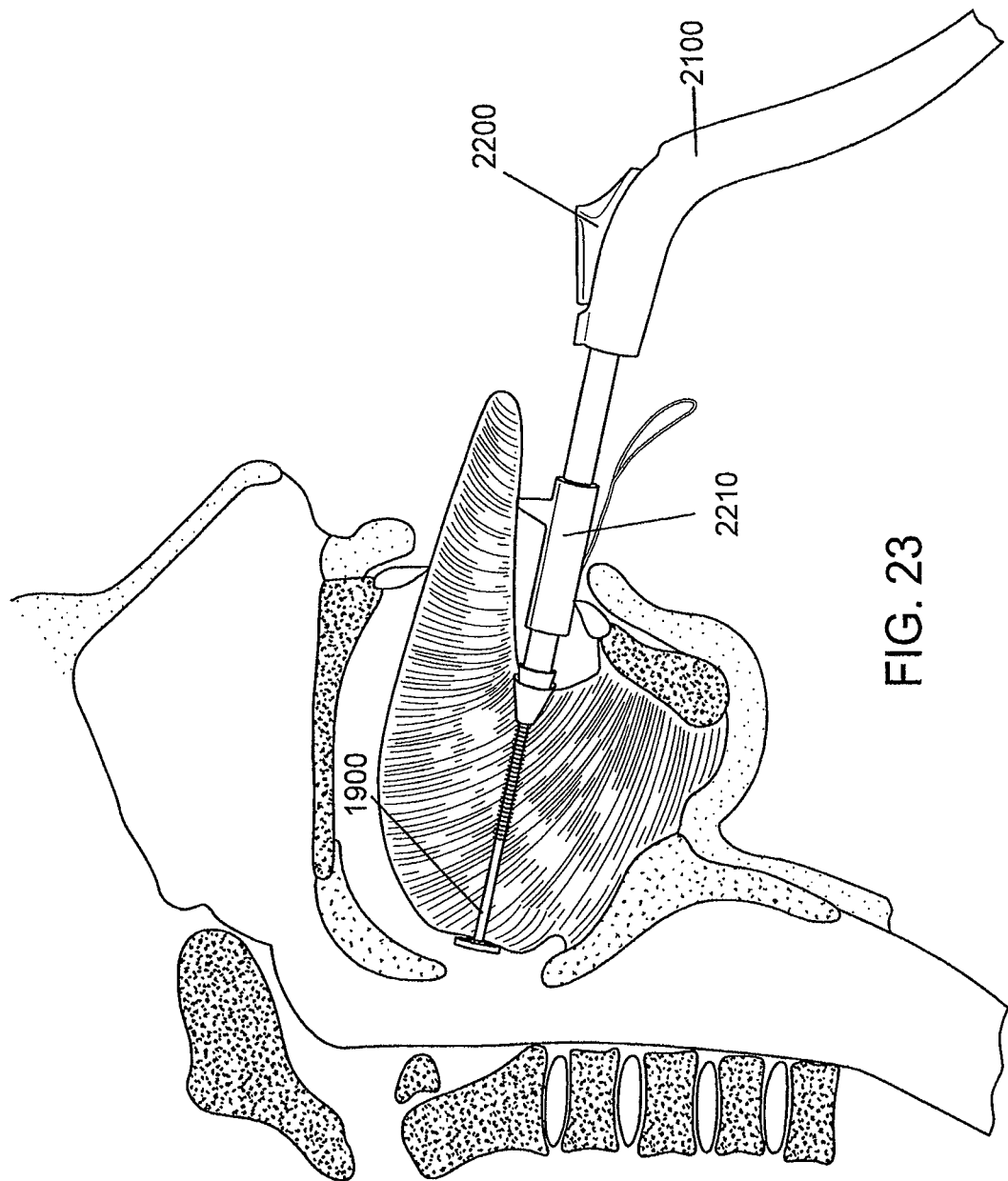
FIG. 23 is a schematic illustration of unlocking the anchor using a locking and tensioning tool, according to an illustrative embodiment of the invention.

FIG. 23 is a schematic illustration of unlocking the anchor member 1900 using a locking and tensioning tool 2100, according to an illustrative embodiment of the invention. A doctor can use the thumb lock 2200 to lock and unlock the anchor member 1900. For example, when the doctor pushes the thumb lock 2200 backward, the locking mechanism 2210 is in the forward position and the anchor member 1900 is unlocked.

Figure 24:
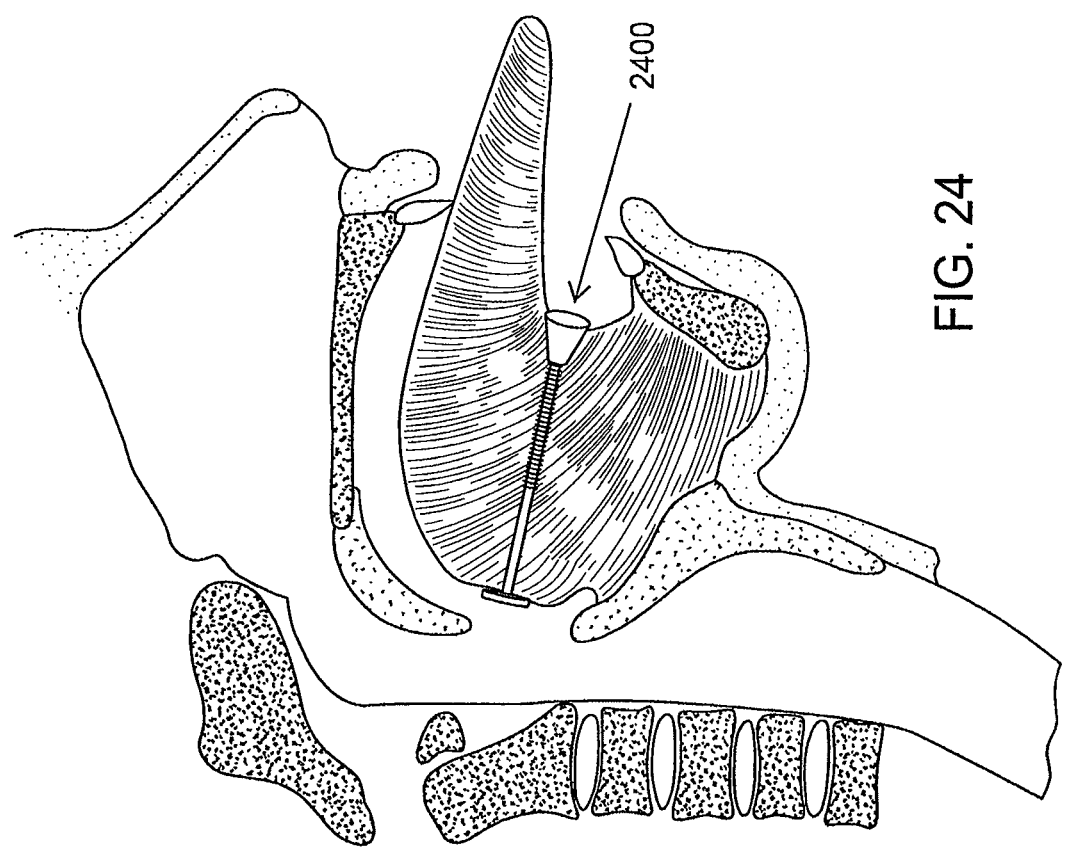
FIG. 24 is a schematic illustration of a tissue retractor in place in a soft issue, according to an illustrative embodiment of the invention.

FIG. 24 is a schematic illustration of a tissue retractor 2400 in place in a soft issue, according to an illustrative embodiment of the invention. After the implantable tissue retractor is inserted into the soft tissue of a patient, the excess portions of the implantable tissue retractor, including a portion of the shaft if necessary, and the removable coupler, are removed.

In some embodiments, a patient needs to have two tissue retractors inserted into the soft tissue to cure OSAS. For example, a patient may have an excessive amount of soft tissue blocking the patient's airway. In some situations, a patient will require two or more tissue retractors to be implanted at different locations to obtain the proper amount of force along the soft tissue and to place the force in the correct location(s). In some embodiments, the two tissue retractors that are used will be similar and in other embodiments the two tissue retractors that are used will be different.

In the situation where two tissue retractors are implanted into the soft tissue of a patient, the steps described in FIGS. 13-24 are repeated a second time. For example, after a first tissue retractor is inserted into the soft tissue of a patient, a tissue retractor implantation device can be inserted into a second location of a soft tissue located in a patient's oral cavity or pharynx. The tissue retractor implantation device includes a mechanical coupler. A second implantable tissue retractor is inserted into the oral cavity or pharynx. In some embodiments, a tissue retractor holder is used to insert the second implantable tissue retractor into the oral cavity or pharynx. The second implantable tissue retractor comprises a second shaft, a second retractor member disposed at or near a first end of the shaft, and a second removable coupler disposed at or near a second end of the shaft. The second removable coupler is engaged. In some embodiments, the second removable coupler is engaged by the mechanical coupler of the tissue retractor implantation device. The mechanical coupler of the tissue retractor implantation device is withdrawn to secure at least a portion of the second implantable tissue retractor within the soft tissue. A second anchor member is secured to the second end of the second shaft of the second implantable tissue retractor. The second implantable tissue retractor is thus secured within the soft tissue of the patient. Any excess second shaft and the second removable coupler are removed.

In some embodiments, a patient needs to have two different tissue retractors that have a single retractor member. This embodiment is particularly useful if the retractor head is off center from the shaft. For example, after a first tissue retractor is inserted into the soft tissue of a patient, a tissue retractor implantation device is inserted into a second location of a soft tissue located in a patient's oral cavity or pharynx. The tissue retractor implantation device includes a mechanical coupler. A second implantable tissue retractor is inserted into the oral cavity or pharynx. In some embodiments, a tissue retractor holder is used to insert the second implantable tissue retractor into the oral cavity or pharynx. The second implantable tissue retractor comprises a second shaft and a second removable coupler disposed at or near a second end of the shaft. The second removable coupler is engaged. In some embodiments, the second removable coupler is engaged by the mechanical coupler of the tissue retractor implantation device. The mechanical coupler of the tissue retractor implantation device is withdrawn to secure at least a portion of the second implantable tissue retractor within the soft tissue. A first end of the second implantable tissue retractor is secured to the first retractor member of the first implantable tissue retractor. A second anchor member is secured to the second end of the second shaft of the second implantable tissue retractor. The second implantable tissue retractor is thus secured within the soft tissue of the patient. Any excess second shaft and the second removable coupler are removed.

The invention also relates to a method of retensioning a tissue retractor. In some instances, a surgeon or patient will want to adjust the tension of the tissue retractor. For example, the patient may be uncomfortable at a particular tension and will ask that the tension be adjusted. A surgeon may find that a particular tension is not enough to cure OSAS and will adjust the tension accordingly.

To retension a tissue retractor, a tissue retractor is located within the soft tissue of a patient. The tissue retractor comprises a retractor member located at or near a first end of a shaft and an anchor member located at or near a second end of the shaft. The anchor member is loosened. In some embodiments, the anchor member is loosened using a locking and tensioning tool. In other embodiments, the surgeon loosens the anchor member with his/her fingers. An amount of securing force is established by adjusting the length of the shaft between the retractor member and the anchor member. The anchor member is resecured to the shaft of the tissue retractor. In some embodiments, the anchor member is resecured using a locking and tensioning tool. In other embodiments, the surgeon resecures the anchor member with his/her fingers.

In some embodiments, the anchor member is comprised of a locking member and a pad. In these embodiments, the tissue retractor can be retensioned by removing or replacing a pad. When the pad is removed or if the pad is replaced with a thinner pad, the tension is decreased. When the pad is replaced with a thicker pad, the tension is increased.

The invention also relates to methods of replacing tissue retractors. In some instances, the tissue retractor will wear out over time. For example, the tissue retractor may not be able to obtain the correct tension because the shaft has been stretched out. In some instances the tension will need to be reduced but there is an insufficient amount of shaft left to loosen the tension.

To replace a first tissue retractor, a tissue retractor is located within the soft tissue of a patient. The first tissue retractor comprises a first retractor member located at or near a first end of a first shaft and a first anchor member located at or near a second end of the first shaft. The first anchor member is removed. The first tissue retractor is extracted from the soft tissue of the patient. A conduit is located where the first tissue retractor was extracted from the soft tissue of the patient. A second tissue retractor is implanted along the conduit of the soft tissue of the patient. The second tissue retractor has a second shaft and a second retractor member located at or near a first end of the second shaft. An amount of securing force is established against the soft tissue by adjusting a length of the second shaft. A second anchor member is secured to the second shaft of the second tissue retractor.

In some embodiments the second tissue retractor also comprises a second removable coupler. The second tissue retractor can be implanted following the same steps as described in FIGS. 13-24.

Figure 25:
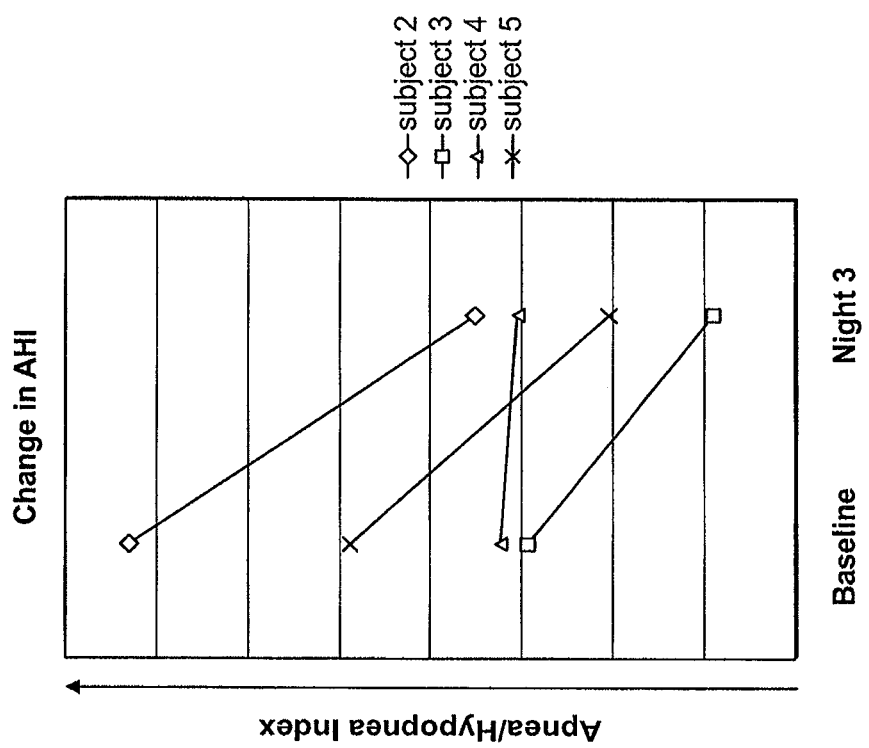
FIG. 25 is a graphical illustration of a change in apnea/hyponea index, according to an illustrative embodiment of the invention.

FIG. 25 is a graphical illustration showing a change in apnea/hypopnea index, according to illustrative embodiments of the invention. The apnea/hypopnea index ("AHI") measures the severity of both apneas and hypopneas including sleep disruptions and desaturations of oxygen in the blood. The index is calculated by dividing the number of apneas and hypopneas by the total number of hours of sleep. A higher AHI means an individual had more apneas and hypopneas than a lower AHI. FIG. 25 shows a change in AHI for four different patients. Each patient had the same tissue retractor design implanted in the patient's tongue for the same amount of time, according to the embodiments of the invention. Moreover, the same surgeon implanted the tissue retractors in each patient at the same hospital. The same facility monitored each patient's AHI. All four individuals started with a higher AHI before the tissue retractor was implanted. Three of the four individuals had a dramatic decrease in AHI after three nights using the tissue retractor.

Figure 26:
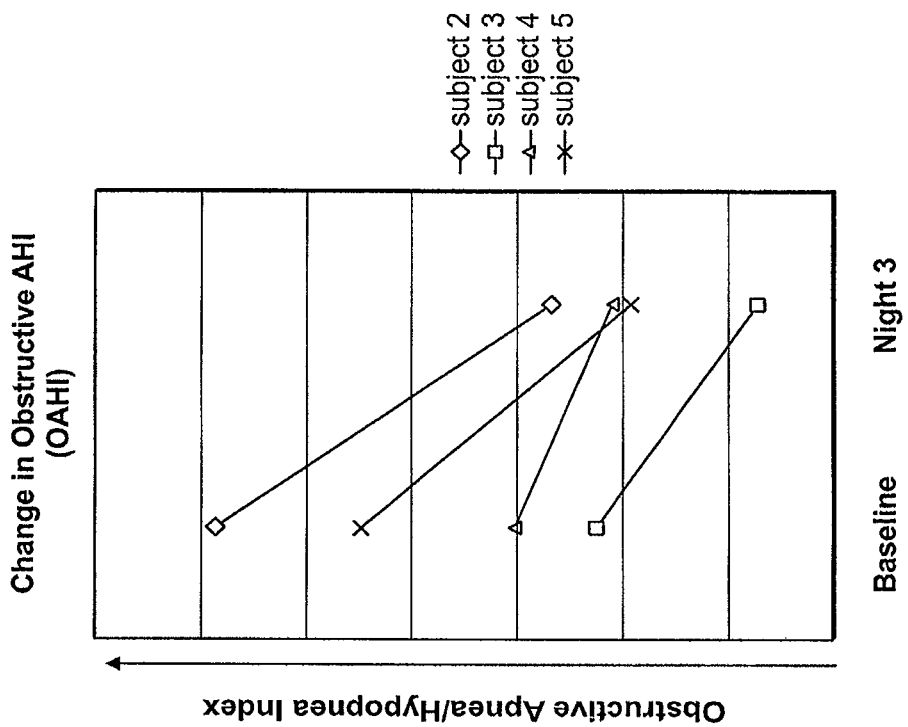
FIG. 26 is a graphical illustration of a change in obstructive apnea/hyponea index, according to an illustrative embodiment of the invention.

FIG. 26 is a graphical illustration showing a change in obstructive apnea/hypopnea index ("OAHI"), according to illustrative embodiments of the invention. OAHI is a measurement used to eliminate central apnea events (i.e., non obstructive apnea events) from the sleep study reading of AHI, which includes all apnea events. The index is calculated by dividing the number of obstructive apneas and hypopneas by the total number of hours of sleep. A higher OAHI means an individual had more obstructive apneas and hypopneas than a lower OAHI. The same four patients that were tested for AHI in FIG. 25 were tested for OAHI in FIG. 26. All four patients showed a dramatic decrease in OAHI after the tissue retractor was implanted into the patient's tongue.

Figure 27:
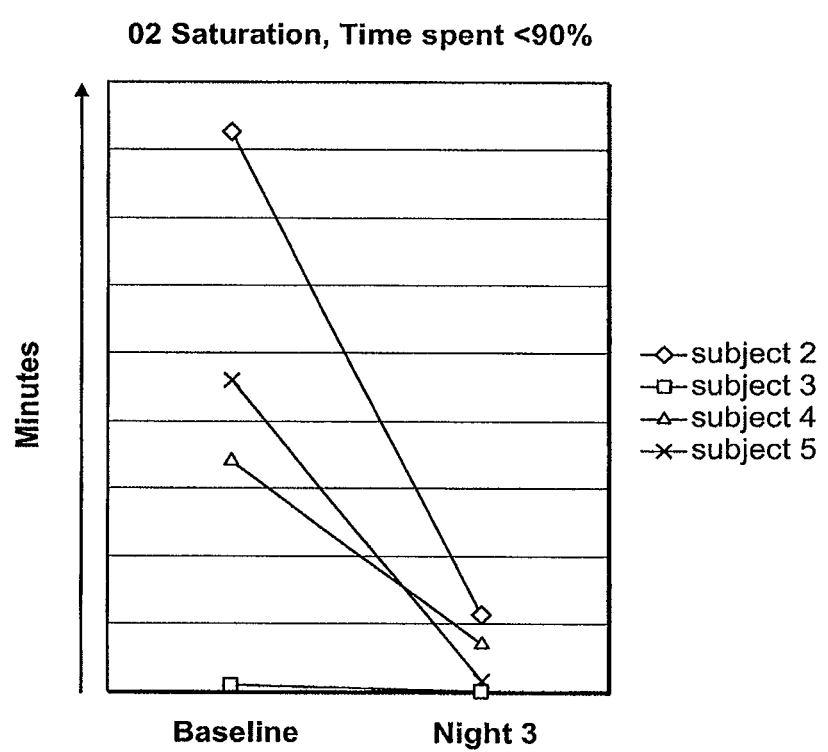
FIG. 27 is a graphical illustration of a change in oxygen saturation, according to an illustrative embodiment of the invention.

FIG. 27 is a graphical illustration illustrating a change in oxygen saturation for these four patients, according to illustrative embodiments of the invention. This graph measures the amount of time each patient has an oxygen saturation less than 90%. The same four patients that were tested for AHI in FIG. 25 and for OAHI in FIG. 26 were tested for oxygen saturation in FIG. 27. Three of the four patients showed a dramatic decrease in the amount of time the patient spent with an oxygen saturation of less than 90%. Patient 3 did not show a dramatic decrease because patient 3 already started with a minimal amount of time spent at less than 90% oxygen saturation.

Implanting a tissue retractor according to the embodiments of the invention, is a treatment that continues over a long period of time. The testing conducted on the patients as shown in FIGS. 25-27 was only carried out for three days. As FIGS. 25-27 show, the patients experience dramatic decreases in the number of apneas and hypopneas and obstructive apneas and hypopneas. It is expected that the results will get better as the device is implanted for longer periods of time. For example, one common symptom of OSAS is acid reflux which causes inflammation of the vocal cords and nasal mucosa. It could take 30 days to fully recover from the effects of acid reflux. Therefore, it is likely that patients will not see the full benefit of the tissue retractor treatment for 30 days or more. However, even after just three days with the tissue retractor, the four patients saw dramatic benefits as shown by FIGS. 25-27.

While the invention has been particularly shown and described with reference to specific preferred embodiments, it should be understood by those skilled in the art that various changes in from and detail may be made therein without departing from the spirit and scope of the invention as defined by the following claims.

What is claimed is:

1. An implantation assembly for insertion of an implantable tissue retractor, the implantation assembly comprising:
    an implantation device comprising:
        a shaft having a pointed end and a second end;
        a mechanical coupler near the pointed end of the shaft, the mechanical coupler adapted to couple with a removable coupler of the tissue retractor; and
        a handle at the second end; and
    a tissue retractor holder comprising:
        a handle;
        a retainer disposed at a distal end of the handle of the tissue retractor holder for releasably retaining the removable coupler of the tissue retractor; and
        a detainer positioned along the handle of the tissue retractor holder for releasably engaging the tissue retractor,
    wherein the retainer is adapted to provide a force to a soft tissue, the force preventing deformation of the soft tissue when the implantation device is inserted into an opposite side of the soft tissue.

2. The implantation assembly of claim 1, wherein the mechanical coupler comprises a cleft.

3. The implantation assembly of claim 1, wherein the mechanical coupler comprises a suture, a magnet, a vacuum, an adhesive, a screw, or a hook.

4. The implantation assembly of claim 1, wherein the removable coupler of the tissue retractor comprises a suture, a magnet, a vacuum, an adhesive, a screw, or a hook.

5. The implantation assembly of claim 1, wherein the implantation device further comprises a releasable locking member located at or near the mechanical coupler.

6. The implantation assembly of claim 5, wherein the releasable locking member is a sheath, the sheath sized to fit over the shaft and configured to hinder unintentional disengagement of the removable coupler of the tissue retractor.

7. The implantation assembly of claim 1, wherein the handle of the implantation device contains a tension meter, the tension meter capable of measuring the tension applied to a shaft of the tissue retractor.

8. The implantation assembly of claim 1, wherein the retainer comprises a first forked arm and a second forked arm extending from the distal end of the handle of the tissue retractor holder.

9. The implantation assembly of claim 8, wherein a distal end of the first forked arm is connected to a distal end of the second forked arm forming a continuous surface.

10. The implantation assembly of claim 1, wherein the detainer comprises at least one of a groove, a clamp, and a clip.

11. The implantation assembly of claim 1, wherein the tissue retractor holder further comprises a guard disposed at or near the retainer, the guard configured to impede excessive progression of the implantation device.

12. The implantation assembly of claim 1, wherein the handle of the tissue retractor holder is curved at or near the portion of the handle where the handle and the retainer are joined.

* * * * *